(12) United States Patent
Hussein et al.

(10) Patent No.: US 11,322,254 B1
(45) Date of Patent: May 3, 2022

(54) PERSONAL WELLNESS AND WELLBEING INFORMATION SYSTEM

(71) Applicants: Abdulkadir Mohamed Hussein, Tempe, AZ (US); Hussein Mohamed Hussein, Tempe, AZ (US)

(72) Inventors: Abdulkadir Mohamed Hussein, Tempe, AZ (US); Hussein Mohamed Hussein, Tempe, AZ (US)

( * ) Notice: Subject to any disclaimer, the term of this patent is extended or adjusted under 35 U.S.C. 154(b) by 0 days.

(21) Appl. No.: 17/341,231

(22) Filed: Jun. 7, 2021

(51) Int. Cl.
| | |
|---|---|
| *G16H 40/67* | (2018.01) |
| *G06F 1/16* | (2006.01) |
| *G01N 33/00* | (2006.01) |
| *A61B 5/00* | (2006.01) |
| *A61B 5/0205* | (2006.01) |
| *G06F 3/0484* | (2013.01) |
| *G06F 3/04847* | (2022.01) |

(52) U.S. Cl.
CPC ............ *G16H 40/67* (2018.01); *A61B 5/0022* (2013.01); *A61B 5/02055* (2013.01); *A61B 5/6826* (2013.01); *A61B 5/6831* (2013.01); *A61B 5/6898* (2013.01); *A61B 5/7246* (2013.01); *A61B 5/746* (2013.01); *G01N 33/0063* (2013.01); *G06F 1/1656* (2013.01); *A61B 2560/0214* (2013.01); *A61B 2560/0247* (2013.01); *A61B 2560/0462* (2013.01); *G06F 3/04847* (2013.01)

(58) Field of Classification Search
CPC ........ G16H 40/67; G16H 50/00–50/80; A61B 5/0022; A61B 5/02055; A61B 5/6826; A61B 5/6831; A61B 5/6898; A61B 5/7246; A61B 5/746; A61B 2560/0214; A61B 2560/0247; A61B 2560/0462; G01N 33/0063; G06F 1/1656; G06F 3/04847

See application file for complete search history.

(56) References Cited

U.S. PATENT DOCUMENTS

| | | | |
|---|---|---|---|
| 10,424,412 B2 * | 9/2019 | Huang | A61B 5/7465 |
| 2019/0237204 A1 * | 8/2019 | Huang | G16H 80/00 |
| 2020/0297955 A1 * | 9/2020 | Shouldice | G16H 40/67 |
| 2021/0169417 A1 * | 6/2021 | Burton | A61B 5/02055 |

* cited by examiner

*Primary Examiner* — Jonathan T Kuo
(74) *Attorney, Agent, or Firm* — Booth Udall Fuller, PLC

(57) ABSTRACT

System for the purpose of realizing wellness and wellbeing that enables users to define personal wellness and wellbeing objectives that establish the scope of contextualizing user specific condition. The system collects and co-analyzes ambient pollution and physiological biomarkers data that include ambient airborne pollution, electric field radiation pollution, magnetic field radiation pollution, RF signal radiation pollution, temperature changes, relative humidity, and users' physiological biomarkers. The system operates in three modes: interactive, passive, and physical mode, and it uses range extender remote ambient pollution monitors to cover any desired indoor-space. The system is built on a universal holder that expands and retracts both vertical and horizontal dimensions to fit as a protective case and sleeve for various sizes of smartphone and handheld devices. The system guides and orchestrates users' deliberate effort of achieving target wellness and wellbeing objectives, and it informs any adverse condition to the users' wellness and wellbeing.

15 Claims, 19 Drawing Sheets

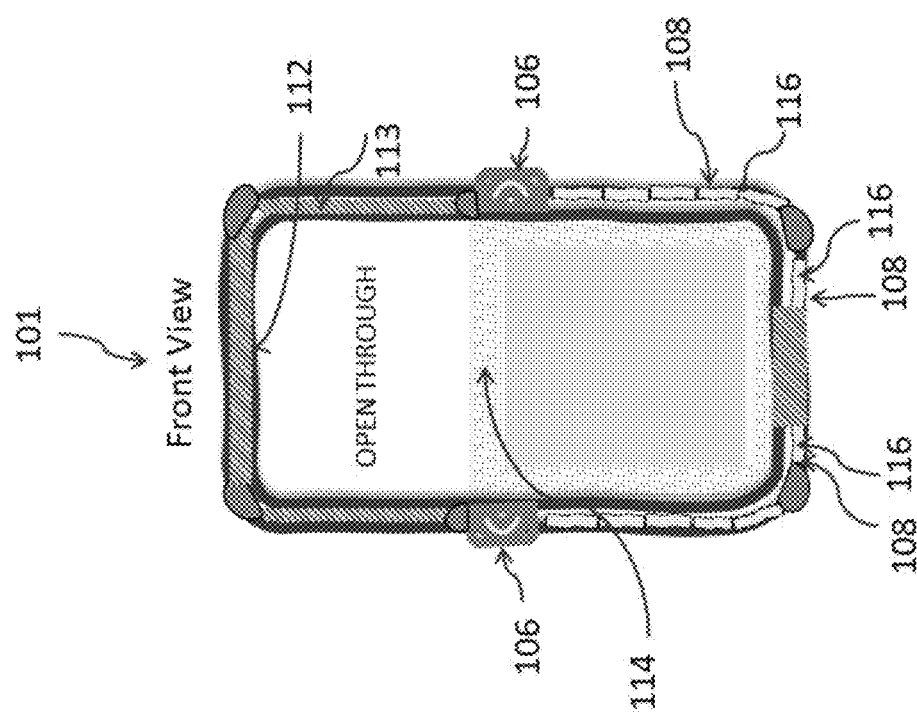

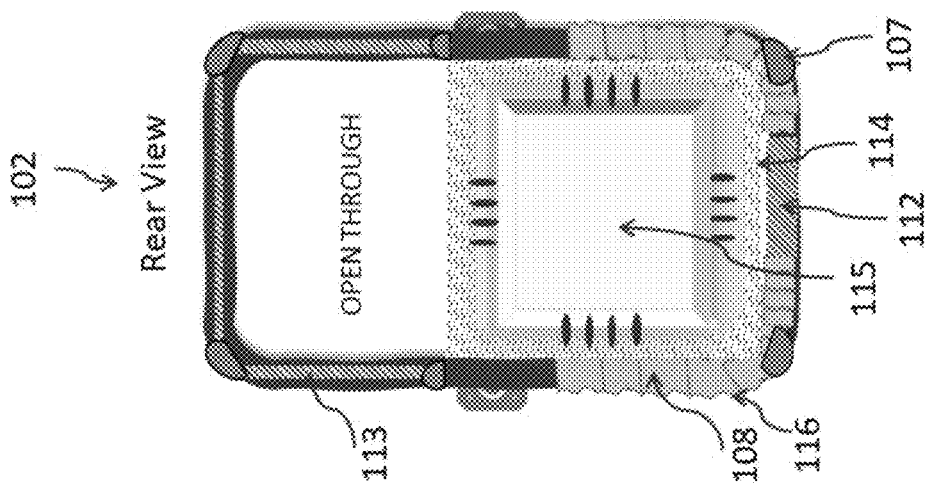

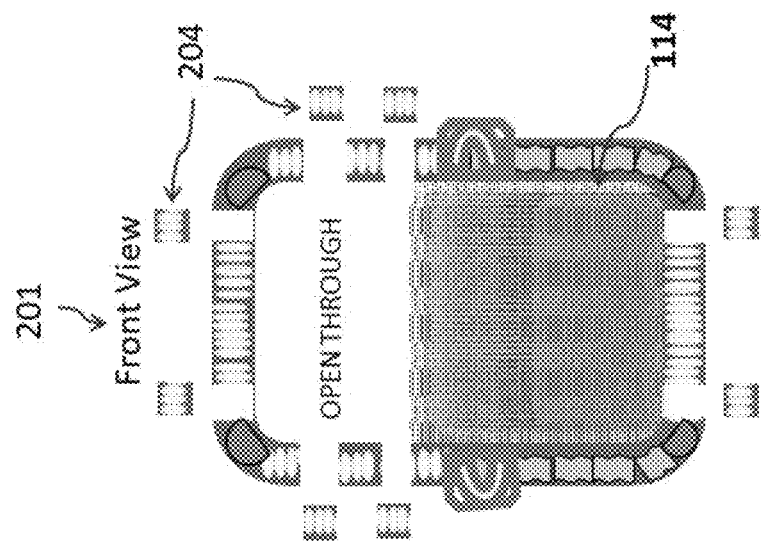

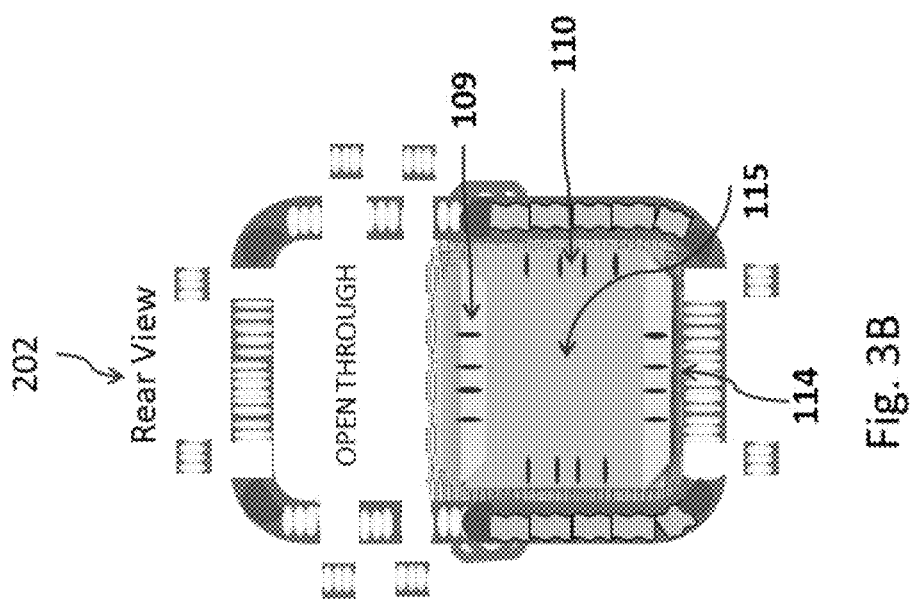

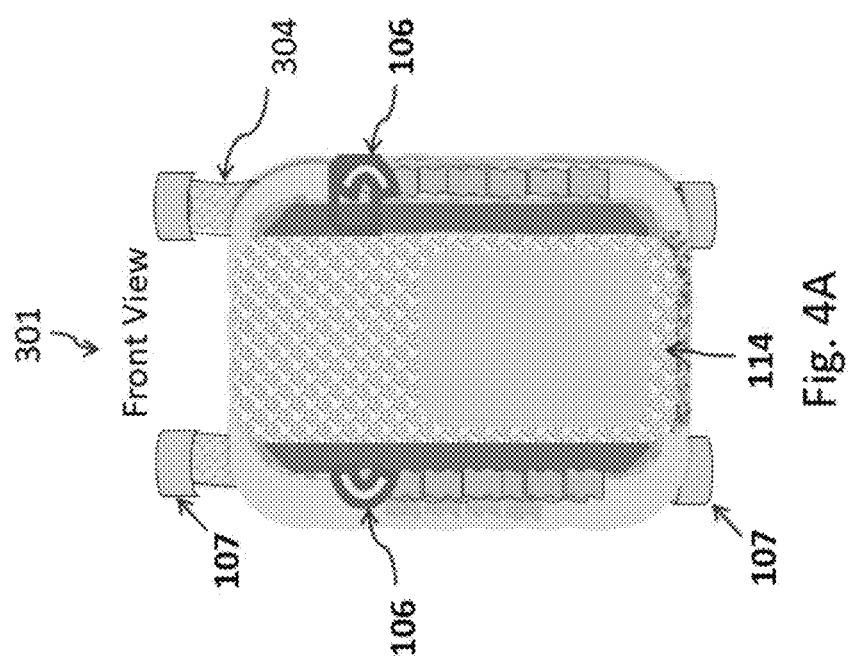

PERSONAL WELLNESS AND WELLBEING INFORMATION SYSTEM

TECHNICAL FIELD

Aspects of this document relate generally to a handheld device for wellness and wellbeing, and more specifically to a personal wellness and wellbeing information system in a protective case and sleeve for various sizes of smartphones and handheld devices that collects and co-analyzes pollution exposure from user's ambient and physiological biomarkers from contacts with user's hand-palm and fingers.

BACKGROUND

In various estimates, people spend 80% to 90% of their time in indoors and the ambient pollution condition of the indoor-space becomes an important factor of their wellness and wellbeing condition. There are continuous efforts at local, national, and international public health and environmental agencies to establish safety guidelines and standards for exposure limits to ambient pollution concentrations. Guidelines and standards continuously evolve and global agencies like World Health Organization (WHO) and International Commission on Non-Ionizing Radiation Protection (ICNIRP) compile global research data. In addition, there are non-profit organizations like BioInitiative organization (bioinitiative.org) and Building Biology Institute (buildingbiology.com) that recommend research-based evidence that focus on biological impact of various ambient pollution condition exposures to the wellness and wellbeing of the people.

Unfortunately, average person might not be aware of these health and safety guidelines and more importantly the people have no information about their daily exposures to potentially adverse ambient pollutions that they might be experiencing potentially prolonged period of time. The increase of man-made pollution exposure in the indoor-space poses significant risk to wellness and wellbeing. Therefore, there is a need for the people to become aware of the ambient pollution conditions of their indoor-space where they live or work or study or spend time during their daily lives that could have significant adverse effect to their wellness and wellbeing. An informed person will be in a position to make an informed decision about the risks of exposure to ambient pollution that could have impact to wellness and wellbeing. Although limited examples of in-home air quality monitoring devices exist, and larger examples of outdoor air quality monitoring devices exist, they are all limited in their usefulness because of size and configuration to monitoring a particular type of air quality in a particular stationary location.

SUMMARY

Aspects of this document relate to a wellness and wellbeing information system may comprise a holder for a protective case and sleeve configured to couple with and protect an electronic handheld device having a user interface, wherein the protective case and sleeve are adjustable to fit each of a plurality of different electronic handheld devices, a statistical data comparator configured to communicate with the protective holder to anonymously compare statistical averages of ambient pollution exposures and physiological biomarker data stored in the protective holder to receive a request from a user and to respond an outcome to the user, and a sensor device affixed to the protective case, communicatively coupled to the electronic handheld device, and controllable through the user interface, the sensor device having processing function and an internal battery, a plurality of sensors coupled to the internal battery, and controlled airflow through a first vent and a second vent each extending through the sensor device and each configured to supply ambient air to the plurality of sensors, wherein the first vent is perpendicular to the second vent; wherein the sensor device is configured to sense an orientation of the protective holder and select one of the first vent and the second vent as a source of ambient air based on which of the first vent and the second vent is closest to a vertical orientation; wherein the sensor device is configured to detect any contact of hand-palm or fingertips and select any validated stable contact between the user's hand-palm and fingers and the front-end of the plurality of sensor devices on the perimeter of the protective holder; wherein the plurality of sensors is configured to collect data regarding ambient pollution conditions and physiological biomarker conditions of a user and communicate the contextual information to the electronic handheld device; wherein the ambient pollution conditions include at least one of ambient airborne pollution, ambient electric field radiation pollution, ambient magnetic field radiation pollution, and ambient radiofrequency signal radiation pollution; wherein the physiological biomarker conditions include at least one of a cardiovascular activities, autonomic coherence, respiration, blood oxygen saturation, microvascular blood flow, fingernail cortisol, stress, fatigue, body's capacity to fight stressors and body thermoregulations; wherein the information system is configured to operate in at least three operation modes, the operation modes comprising an interactive mode wherein the information system collects data regarding at least one of the ambient pollution conditions and the physiological biomarker conditions in response to a query by the user, a passive mode wherein the information system collects the data regarding at least one of the ambient pollution conditions and the physiological biomarker conditions at predetermined periodic intervals without any user awareness, and a physical mode wherein the information system continuously collects data regarding at least one of the ambient pollution conditions and the physiological biomarker conditions; and wherein the information system autonomously collects and processes the data regarding at least one of the ambient pollution conditions and the physiological biomarker conditions at a user configured periodic cycle provided the user is authenticated in passive mode even when the electronic handheld device is turned off, and the user interface (App) is shutdown.

Particular embodiments may comprise one or more of the following features. A range extender configured to extend an indoor coverage distance over which the information system is capable of measuring the ambient pollution conditions. An elastic secured biosensor configured to fit over a finger of the user and provide measurements of the physiological biomarker conditions of the user when the monitoring system is in the interactive mode. A biosensor strap configured to wrap around a limb of the user, detect an artery within the user, indicate biosensor alignment with the artery, and attach the monitoring system to the user for continuous data collection when the monitoring system is in the physical mode. The information system may be configured to communicate user selected data to a pre-arranged third party and provides a secure interface wherein only the user is allowed to send the user selected data stored in the protective holder to a third party. The user interface may be configured to allow the user to set exposure limits for the ambient pollution conditions and alert the user when the exposure limits are reached. The user interface may be configured to allow the user to set biomarker ranges for the physiological biomarker conditions and alert the user when a selected physiological biomarker condition is out of range. Users' request for comparison of statistical averages of ambient pollution exposures and physiological biomarker conditions stored in their holders may be compared with statistical averages pooled from other participating users and benchmark data.

According to an aspect of the disclosure, a wellness and wellbeing information system may comprise a holder for protective case and sleeve configured to couple with and protect an electronic handheld device having a user interface, a statistical data comparator configured to communicate with the protective holder to anonymously compare statistical averages of ambient pollution exposures and physiological biomarker data stored in the protective holder to receive a request from a user to compare user selected statistical averages of ambient pollution exposures and physiological biomarker data stored in the protective holder with information system's benchmark data, and respond with a result to the user request, a range extender configured to extend the indoor coverage over which the information system is capable of measuring the ambient pollution conditions, and a sensor device affixed to the protective holder, communicatively coupled to the electronic handheld device, and controllable through the user interface, the sensor device having an internal battery, a processing function and a plurality of sensors coupled to the internal battery; wherein the plurality of sensors is configured to collect data regarding ambient pollution conditions and physiological biomarker conditions of a user and communicate the information to the electronic handheld device; and wherein the information system is configured to operate in at least one of an interactive mode wherein the information system collects data regarding at least one of the ambient pollution conditions and the physiological biomarker conditions in response to a query by the user, a passive mode wherein the information system collects data regarding the ambient pollution conditions and the physiological biomarker conditions at predetermined periodic intervals, and a physical mode wherein the information system continuously collects data regarding at least one of the ambient pollution conditions and the physiological biomarker conditions.

Particular embodiments may comprise one or more of the following features. The information system may further comprise a range extender configured to extend an indoor coverage distance over which the information system is capable of measuring the ambient pollution conditions. The ambient pollution conditions may include at least one of ambient airborne pollution, ambient electric field radiation pollution, ambient magnetic field radiation pollution, and ambient radiofrequency signal radiation pollution.

According to an aspect of the disclosure, a wellness and wellbeing information system may comprise a sensor device communicatively coupled to an electronic handheld device having a user interface configured to control the sensor device, the sensor device having a plurality of sensors configured to collect data regarding ambient pollution conditions and physiological biomarker conditions of a user and communicate the information to the electronic handheld device, and a statistical data comparator configured to receive a request to compare a user selected statistical average of ambient pollution exposures and physiological biomarker conditions data with benchmark data within the information, and responds an outcome to the requestor; wherein the information system is configured to operate in at least one of an interactive mode wherein the information system collects data regarding at least one of the ambient pollution conditions and the physiological biomarker conditions in response to a query by the user, a passive mode wherein the information system collects data regarding the ambient pollution conditions and the physiological conditions at predetermined periodic intervals, and a physical mode wherein the information system continuously collects data regarding at least one of the ambient pollution conditions and the physiological conditions.

Particular embodiments may comprise one or more of the following features. A holder for protective case and sleeve configured to couple with and protect the electronic handheld device, wherein the sensor device is affixed to the protective case and sleeve. The information system may be configured to operate in at least two of the interactive mode, the passive mode, and the physical mode. The ambient pollution conditions may include at least one of ambient airborne pollution, ambient electric field radiation pollution, ambient magnetic field radiation pollution, and ambient radiofrequency signal radiation pollution. The physiological biomarker conditions may include at least one of a cardiovascular activities, autonomic coherence, respiration, blood oxygen saturation, microvascular blood flow, fingernail cortisol, stress, fatigue, body's capacity to fight stressors and body thermoregulation. A range extender configured to extend the indoor coverage over which the monitoring system is capable of measuring the ambient pollution conditions. The user interface may be configured to allow the user to set thresholds for exposure limits for the ambient pollution conditions and physiological biomarker ranges, and alert the user when the thresholds are reached. The information system may be configured to autonomous collect and process data at a user configured periodic cycle provided the user is authenticated in passive mode, and the information system is configured to continue data collection and processing when the electronic handheld device is not paired with the protective holder, the electronic handheld device is turned off, and the user interface (App) is shutdown.

The foregoing and other aspects, features, applications, and advantages will be apparent to those of ordinary skill in the art from the specification, drawings, and the claims. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112(f). Moreover, even if the provisions of 35 U.S.C. § 112(f) are invoked to define the claimed aspects, it is intended that these aspects not be limited only to the specific structure, material or acts that are described in particular embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those of ordinary skill in the art from the specification, drawings, and the claims.

BRIEF DESCRIPTION OF THE DRAWINGS

Implementations will hereinafter be described in conjunction with the appended drawings, where like designations denote like elements, and:

FIGS. 2A-2E depict an embodiment of a wellness and wellbeing information system that expands in a case formfactor.

FIGS. 3A-3C depict an embodiment of a wellness and wellbeing information system with a link-extension that link-extends in a case formfactor.

FIGS. 4A-4C depicts an embodiment of a wellness and wellbeing information system that expands in a sleeve formfactor.

Figure 1A:
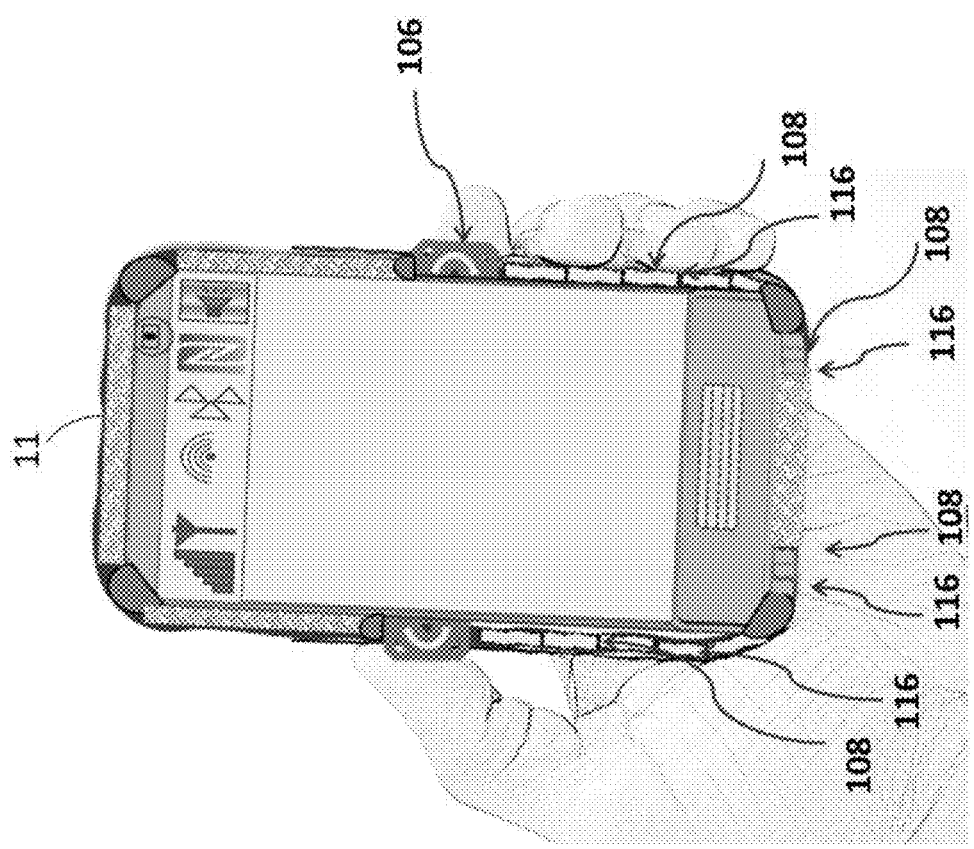
FIGS. 1A-1C illustrate an embodiment of a wellness and wellbeing information system fitted with smartphone and used in passive, interactive and physical mode.

One of ordinary skill in the art will appreciate that elements in the figures are illustrated for simplicity and clarity and have not necessarily been drawn to scale. For example, the dimensions of some of the elements in the figures may be exaggerated relative to other elements to help to improve understanding of implementations.

DETAILED DESCRIPTION

This disclosure, its aspects and implementations, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

While this disclosure includes a number of implementations that are described in many different forms, there is shown in the drawings and will herein be described in detail particular implementations with the understanding that the present disclosure is to be considered as an exemplification of the principles of the disclosed methods and systems, and is not intended to limit the broad aspect of the disclosed concepts to the implementations illustrated.

In the following description, reference is made to the accompanying drawings which form a part hereof, and which show by way of illustration possible implementations. It is to be understood that other implementations may be utilized, and structural, as well as procedural, changes may be made without departing from the scope of this document. As a matter of convenience, various components will be described using exemplary materials, sizes, shapes, dimensions, and the like. However, this document is not limited to the stated examples and other configurations are possible and within the teachings of the present disclosure. As will become apparent, changes may be made in the function and/or arrangement of any of the elements described in the disclosed exemplary implementations without departing from the spirit and scope of this disclosure.

Although there might be air quality monitoring devices in-use in certain homes, these devices are not carried with the users wherever they might be throughout the day and their usefulness is limited to the specific location they are placed. Unless users carry them all the time, which is impractical for most of the people, users have no continuous and adequate information about their ambient pollution condition wherever they are. Also, conventional current technology, users would need to carry a separate wearable device to be able to get information about their health. However, without accounting for users' ambient pollution exposure temporal condition and over time, meaningful monitoring and assessment of the users' short and long-term wellness and wellbeing in relation to their environmental quality cannot be achieved.

Interest in devices for consumer-grade health tracking continue to evolve with the miniaturization of the relevant sensor technology. Conventional devices collect data through physical contact of the user's body and they are mostly in the form of wearable devices in various formfactor that include patches, chest-bands, rings, watches, paracletes, headbands, cloves, bodysuits, t-shirts, and similar wearable devices. These wearable devices do not provide a solution to the need for a comprehensive and contextualized wellness and wellbeing information because they do not account for the cause and effect of ambient pollution exposure condition of the user. Furthermore, certain wearable devices are limited by their specific purpose, like tracking user's physical exercise activities, that renders them unused the rest of the day when the users are not involved in physical exercises. For the wrist worn watch-based devices, some people might not want to change their preferred watch to a new smartwatch or wrist band to collect biomarker data. Another limitation of the wearable devices is the practical aspect of their formfactor like rings, parcellates, headband, chestband, gloves, etc. that might be discouraging some who are interested in tracking their health state. However, there are users, like athletes, that generally wear these devices for an extended period of time to monitor the status of their performance. There are also certain medical diagnostic applications that place application-specific wearable devices on the body of the patients during a diagnostic period to collect biomarkers data.

Although there appears to be no consensus on the technical meaning of wellness and wellbeing in the literature and in certain cases are still considered to be the same, WHO and USA National Institute of Health (NIH) among other organizations generally point out two dimensions of wellness and wellbeing that are related to subjective and objective aspects of one's health. In the present disclosure, a user's wellness and wellbeing objectives are referred to as an individual's desired outcome of a deliberate effort to aim for and to continuously endeavor to maintain an optimum holistic state that enables a person to navigate the path to achieve the full potential of a fulfilling life. This simply means wellness is viewed much more than the health aspect of a person because a person, for example, might be exposed to a prolonged ambient pollution condition that triggers physiological reactions that could have adverse effects to the person's wellness, like a sleep disorder. As another example, a person might appear to be free of any illness and maintaining physically active lifestyle while suffering from fatigue, or chronic stress, or degrading coherence of heart rhythm, etc. due to environmental factors. Wellness, therefore, is defined as an individual's optimum holistic state that continuously accounts for and contextualizes both person's continuous ambient pollution condition and physiological biomarker condition.

For this disclosure, wellbeing is viewed objectively as a precondition to achieve the full potential in life. Although no fundamental change of a person's baseline condition has yet appeared a person's cumulative experience becomes critical aspect of maintaining and achieving a fulfilling live. For example, a person who is doing everything according to a popular healthy living theme might be exposed to Volatile Organic Compounds (VOC) or Particulate Matter (PM) or other gases in the indoor-space. As result, this person might be experiencing causes of adverse effects to her/his wellbeing, and gradually start deviating from the path of reaching a fulfilling life because once physiological damage to one's baseline condition happens then wellbeing might not be regained at its current state. Another example, a person might be living with an existing precondition like diabetic or heart condition, and certain exposure to ambient pollution in the indoor-space could exacerbate the person's condition and lead to significant impact to the wellbeing objectives of this person. Wellbeing is defined as a contextualized state of long-term sustained condition of an individual who is deliberately seeking to maintain an optimum baseline condition for achieving a fulfilling life.

Because people might be interested in becoming proactive and aiming for wellness and wellbeing, continuous contextualization of individual's ambient pollution exposure experience becomes a critical element for setting and achieving a personal wellness and wellbeing objectives. A contextualized information is expected to encourage people's effort to improve indoor-space air circulation and adjustments to people's routine and ways of life in the indoor-space where they sleep, live and work. For example, a person's use of typical household cleaning materials where the house or the apartment has insufficient ventilation after the use of these cleaning materials could lead to an indoor-space contamination that results in an elevated concentration of Volatile Organic Compounds (VOC) that have adverse effect to the wellness and wellbeing of the people living in it.

Governmental organization like United States Environmental Protection Agency (EPA) and European Commission's Directorate General for Health and Consumers provide details of Sick Building Syndrome that is a term used to describe various adverse conditions affecting people's wellness and wellbeing in the indoor-space. The EPA and EU Commission provide guidelines are meant to rectify the indoor pollution condition. For example, EPA's Indoor Air Facts No. 4 describes Sick Building Syndrome as "occupants experience acute health and comfort effects that appear to be linked to time spent in a building." However, EPA states "No federally enforceable standards have been set for VOCs in non-industrial settings." Although it is practically impossible to fully enforce safety standards in the household where the public risk to the exposure of ambient pollution resulting from indoor-space contaminants is higher, there are currently no adequately effective solution that bring the occupants of the indoor-space as stakeholders and raise their awareness. Embodiments of the present disclosure aim to raise the awareness of the users and to encourage their vested interest to mitigate the indoor-contaminants and any potential adverse effects to wellness and wellbeing.

To highlight variations among the public health standards for exposure limits for indoor-space pollutants, WHO guidelines and USA standards define concentration of PM2.5 exposure not to exceed 25 $\mu g/m^3$ and 35 $\mu g/m^3$ respectively averaged over 24 hours while EU has no explicitly defined limit for PM2.5 over 24 hours period. Similarly, they define concentration of PM10 exposure not to exceed 50 $\mu g/m^3$, 150 $\mu g/m^3$ and 50 $\mu g/m^3$ respectively overaged over one year. There are even variations within a country, for example, state of California defines concentration of PM10 exposure not to exceed 50 $\mu g/m^3$ that is much tighter than the US federal standard of 150 $\mu g/m^3$. The body of scientific literature identify long list of adverse health effects related to indoor PM, especially those with preexisting disease conditions, that include chronic obstructive pulmonary disease, asthma, wheezing, cough, cardiovascular diseases, autonomic nervous system (ANS) imbalance, effects to heart rate (HR) and heart rate variability (HRV), blood pressure (BP), and many more that impact the person's target wellness and wellbeing objectives. Conventionally, however, individuals have no technology or solution for monitoring their actual exposure throughout the day other than at specific locations through general, stationary external monitoring devices.

Similarly, the lack of awareness of the implication of humidity in the indoor-space, where high-humidity condition fosters the growth and spread of molds and aggravates biological contaminants in the indoor-space. Notwithstanding the availability of different kinds of thermostats with built in hygrometer that are capable to accurately monitor the temperature and the relative humidity of the indoor-space, users do not have an adequate and timely information about the implication to their wellness and wellbeing that will facilitate an informed decision to urgently mitigate the condition of their indoor-space. Even if the Internet of Things (IoT) based solutions deliver relative humidity status to the user's smartphone then there is no mechanism to contextualize it with an individual's desire to maintain a user defined wellness and wellbeing objectives. Also, IoT devices exacerbate radiofrequency signal radiation pollution condition in the indoor-space. Particular embodiments of the present disclosure may be configured to evaluate the relative humidity of the indoor-space and overall ambient pollution condition with respect to the user's defined wellness and wellbeing objectives and informs the user any potential risk or adverse effects of current humidity level.

Another neglected pollution exposure risk that effects the wellness and wellbeing of the people relates to the exponential growth of home electric appliances, electronic devices and wireless based networks that deliver capabilities and services that become an integral part of the daily life. These services and capabilities translate to continuous and increased exposure to electric field radiation pollution, magnetic field radiation pollution and radio frequency (RF) radiation pollution in the indoor-space. Another source of ambient radiation pollution that exacerbates the risk of exposure to the electromagnetic field radiation pollution is the proliferation of smart-meters that transmit pulsed signal throughout the day, and other outdoor devices that have different regulatory power transmission limits that are significantly higher than the consumer electronics devices like smartphone phones, laptops, and WiFi routers. Depending on where these outdoor types of transmitting devices are installed i.e., on the side of the house, apartment, or a pole, they are classified and permitted to transmit relatively higher RF power but exacerbate RF radiation pollution condition in the indoor-space. All these lead to continuous exposure to ambient radiation pollution in the indoor-space that could have adverse effects to the wellness and wellbeing of the people. Particular embodiments of the present disclosure may be configured to inform the users the ambient electromagnetic radiation pollution exposure levels and the risk of potential adverse effects to the users' defined wellness and wellbeing objectives.

Health tracking alone could lead to at best incomplete outcome or potentially inaccurate outcome of the status of the person's wellness and wellbeing. For example, the exposure to an elevated concentration of VOC, or Particulate Matter (PM), or allergens to name few have direct effect to the heart rate variability (HRV) and could induce a temporal condition to the dynamic state of the autonomic nervous system (ANS) which is a key parameter of various consumer health tracking applications. Furthermore, prolonged exposure to these pollutants in the indoor-space could have significant adverse effect to the wellness and welling like causing acute respiratory system or mild lung function impairment. Even an elevated temperature of the indoor-space could lead to an increased body heat that reduces the HRV by increasing sympathetic nervous system (SNS) activity. The interaction and the dynamic between a person's ambient condition and physiological condition are complex, however, there is convergence in the body of scientific research around certain causes and effects of ANS that regulates integral functions of key indicators of person's wellness and wellbeing state. The lack of identifying temporal imbalance of the ANS as a result of the adverse effect of a person's ambient pollution exposure could lead to inaccuracies. Particular embodiments of the present disclosure may be configured to account for the person's temporal ambient pollution condition to contextualize the user's wellness and wellbeing.

Particular embodiments of the present disclosure may be configured to enable users to define personal wellness and wellbeing objectives that are used to establish the scope of contextualizing and monitoring user's holistic state. It collects concurrently and co-analyzes data from user's ambient pollution condition and physiological biomarkers condition to monitor the course of achieving the user's wellness and wellbeing objectives. As explained in more detail below, particular embodiments of systems disclosed in the present disclosure adapt to users' specific circumstances including those living with underlying conditions. A wellness and wellbeing information system may be configured to operate in three modes: (1) interactive mode for controlled data collection; (2) passive mode for automatic data collection without user awareness or direct involvement; and (3) physical mode for continuous data collection. An embodiment of the system guides and orchestrates users' deliberate effort of achieving their desired wellness and wellbeing objectives. It tracks ambient pollution condition of the indoor-space, and it informs any ambient condition that have adverse effect to the users' wellness and wellbeing.

Particular embodiments of a wellness and wellbeing information system collect comprehensive data from user's ambient pollution condition and use a number of integrated sensors for various potentially risky conditions resulting—for example, exposures to electric field radiation pollution, magnetic field radiation pollution and RF signal radiation pollution. A wellness and wellbeing information system according to this disclosure may also be configured to collect exposures to concentration of airborne pollution that include gases, volatile organic compounds, allergens, dust mites, pollens, mold spores, upholstery, carpeting, adhesives, particulate matter (PM2.5 and PM10), temperature and relative humidity. Particular configurations may also collect user's physiological biomarkers data using integrated biosensors that are positioned to detect any opportunity of physical contact with the user's hand palm and fingers while gripping to hold on to user's smartphone and handheld device that is fitted with the embodiment. A wellness and wellbeing information system may also be configured to maintain both raw data and processed data securely within the system.

An aspect of the present disclosure includes a wellness and wellbeing information system that expands to both vertical and horizontal dimensions, and it is usable as a protective case (FIG. 2A) and (FIG. 3A) or a protective case configured as a protective sleeve (FIG. 4A) to fit different sizes and configurations of smartphones and handheld devices. A wellness and wellbeing information system enables the users to exchange their smartphones and handheld devices while keeping all historical personal data stored in the wellness and wellbeing information system. In addition to providing a reusability value for being able to fit different kinds and models of smartphones and handheld devices, particular embodiments of the present disclosure may be configured to maintain strict access, user privacy, and continuity of the integrity of the wellness and wellbeing data that is securely stored in the system. Particular embodiments have the added value of eliminating the wasteful footprint of cases and sleeves that are made for specific model of smartphone or handheld device.

Figure 7:
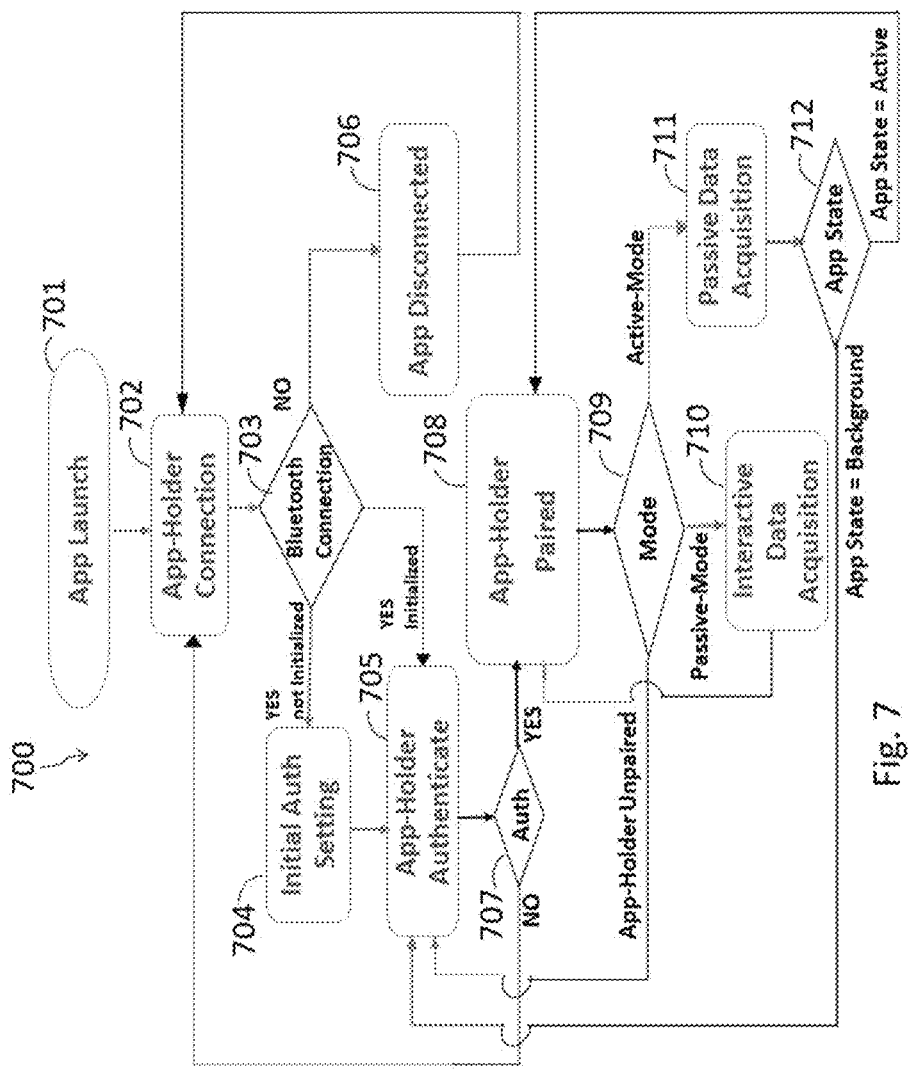
FIG. 7 illustrates the system's security and privacy logic to protect access to personal data.

Particular embodiments used as a protective case communicate with the smartphone and handheld devices via Bluetooth low energy (BLE) that is immediately followed by user self-authentication as a precondition to successfully pair and commence the Bluetooth communication between the universal holder and the system's user application interface (App) running on the smartphones and handheld devices. With reference to FIG. 7, a method of authenticating a user through a wellness and wellbeing information system (700) is illustrated. Whenever the App is launched (step 701) it will prompt user authentication before the user is able to access through the App the personal wellness and wellbeing data stored in the holder system. The holder system and the App will attempt to establish a connection (step 702) and it will transition to one of three possible steps depending on the decision outcome in Bluetooth Connection (step 703). If connection fails then it will transition to App Disconnected (step 706) until the user manually reattempts to establish the connection between the Holder and the App, or the process reattempts after predetermined period of time. If the Bluetooth connection succeeds, then (step 703) checks whether the Holder system's flag that indicates whether the system's authentication is initialized or it is the very first time the App is establishing the Bluetooth connection. If the Holder system's authentication is already initialized then it proceeds to authenticate the user in App-Holder Authenticate (step 705). Otherwise, it proceeds to complete the user's initialization talk for credentials used all future user authentication in Initial Auth Setting (step 704).

All subsequent use of the holder system through the App, App-Holder Authenticate (step 705) will authenticate the user, and depending on the outcome of the decision in Auth (step 707) it will transition back to (step 702) to reattempt App-Holder Connection due to Auth=NO. Otherwise, the process will transition to App-Holder Paired (step 708) that finally allows the user to access the personal wellness and wellbeing data stored in the Holder system through the App depending on the Mode (step 709) which the system is operating. While in the Mode (step 709), if the status become App-Holder Unpaired due to loss of Bluetooth connection then it will transition back to App-Holder Authenticate (step 705), otherwise for Active-Mode it will transition to Interactive Data Acquisition (step 710) and for Passive-Mode it will transition to Passive Data Acquisition (step 711) respectively. The completion of the Interactive Data Acquisition (step 710) will transition back to App-Holder Paired (step 708) to re-enter the Mode (step 709). On the other hand, the completion of the Passive Data Acquisition (step 711) it will transition depending on outcome of the App State (step 712). If the App State indicates that the App is running in the background of the device like a smartphone then it will transition back to App-Holder Authenticate (step 705) to re-authenticate. If the App State indicates it is Active then it will transition back to App-Holder Paired (step 708) to re-enter the Mode (step 709) decision state.

A wellness and wellbeing information system enables the users to reuse their wellness and wellbeing information system for different smartphones and handheld devices by simply swapping the device that is fit with the holder. Although this eliminates the need for different cases or sleeves for different smartphones that lead to wasteful of unused cases and sleeve, the integrity and privacy of the users' data that is stored in the wellness and wellbeing information system becomes important during normal course of using the wellness and wellbeing information system, and it is extremely critical when swapping different smartphones and handheld devices. The embodiment enforces self-authentication during the verification process that is intended to block any access other than the rightful owner of the universal protective case. For example, if a wellness and wellbeing information system fitted with a smartphone is lost or stollen where there is no password protected access active for the locked state of smartphone then two possible scenarios could happen: (a) the user either remotely blocks the smartphone fitted with the wellness and wellbeing information system or requests the service to be suspended through the service provider relatively quickly after losing possession of the smartphone, (b) the user realizes the missing smartphone after some time and then acts to suspend and/or remotely block the smartphone. The authentication process protects both cases.

In case (a), the lost smartphone becomes completely unusable after the user blocks it remotely and no data can be accessed through the wellness and wellbeing information system's user application interface (App) running on the lost smartphone. However, the wellness and wellbeing information system could be taken off from the lost smartphone and refitted into another smartphone. Alternatively, the unauthorized person might attempt to use a different subscriber identity module (SIM) with the lost smartphone that is fitted with the wellness and wellbeing information system if only the service was suspended but the smartphone was still usable. With reference to FIG. 7, the authentication process (700) will fail in (step 704) and in (step 707) respectively. The wellness and wellbeing information system will not pair with any other new App install or SIM card because it was already setup with the smartphone and the SIM of the rightful owner and will require successful integration in (step 705) for reauthenticate to complete the BLE pairing. In the case (b), a lost or stollen smartphone is accessed if it is not passcode locked, and upon launching user application interface (App) and it will fail in (step 707) because the unauthorized user fails to self-authenticate. But if it was already running on the smartphone then (step 712) will catch and block any transition from background to active that will require reauthentication in (step 705) and leads to fail in (step 707).

A wellness and wellbeing information system employs layered protection for the users' personal data while allowing the rightful users to swap their smartphone and handheld device fitted with the wellness and wellbeing information system. For example, authentication process will store and use as part of all future authentication processes the mobile phone number, international mobile subscriber number (IMSI) and the electronic serial number of the device during the initial authentication setup (step 704). Upon swapping the fitted smartphone into the protective case including the processor, the previous smartphone configuration stored in the system will fail to match the new smartphone's electronic serial number with the original serial number stored in the wellness and wellbeing information system. This will trigger a second stage authentication that will interrogate the user to provide additional verification information that the user provided in the original authentication setup (step 704). If the user is successful with the second stage authentication, then the user will be allowed to replace or maintain two active smartphone electronic serial numbers to authenticate for all future authentication process.

However, if the user forgets some of the original verification information or the user requires a reset of the original authentication setup (step 704) then the user will require a fingerprint scan using the elasticated single finger secured biosensor fitting on either side of the wellness and wellbeing information system to recover the authentication process that was registered during the original authentication setup (step 704). The wellness and wellbeing information system may be configured so that a fingerprint can only be registered once for the life of the wellness and wellbeing information system during the very first setup process that makes the wellness and wellbeing information system non-transferable due to the privacy and data protection once a user sets up and uses it. The fingerprint matching provides a third possible recovery mechanism for any failed authentication to only the rightful owner. In the extreme case of both fingerprint readers integrated in the single finger secured biosensor fittings failing, the user would have a final interrogation challenge stage if the user had registered the product which is an optional step upon acquiring the product. A detailed interrogation that will cross check and verify user provided product acquisition information will restore access to the universal holder. Only perfect match of the information provided in product registration, or a match above a predetermined level of certainty, can restore any future access to the data stored in the system.

A wellness and wellbeing information system initiates data communication after successfully authenticating and establishing a pairing (step 708) between the wellness and wellbeing information system used as a protective case or sleeve for smartphone and handheld devices and the user application interface (App) running on the devices. The wellness and wellbeing information system operates in passive mode and will initiate user defined periodic data collection cycle and update the user application interface (App) whenever the self-authentication is successfully completed. But when the user selects for interactive mode and active data acquisition (step 711) from user application interface (App), both ambient pollution condition data and the physiological biomarker data are immediately collected and the user application interface (App) is updated for the user's request. At the end of periodic data collection and mode selection (step 709) the wellness and wellbeing information system will return to its rest state (step 708) as long as the state of the (App) that is running on the smartphone and handheld device does not transitions from actively running state to the background state.

When the state of the (App) changes due to the user bring it from background state to active state that enables the users to interact with it then the (App) will reauthenticate (step 707). Reauthentication process from (step 712) to (step 707) provides additional privacy protection whenever the (App) changes from background to interactive state as the user is attempting to engage with the (App) in the smartphone. State change tracking involves various checks and balances that involve machine learning of the rightful owner's use-cases overtime, and unless unusual sequences of interaction with the (App) is detected, the reauthentication will require no additional interrogation from the user in normal course of use.

The method (700) authenticates the user whenever the smartphone and the handheld devices are exchanged to ensure the rightful user is establishing the Bluetooth connection between the wellness and wellbeing information system and the application interface (App) running on the smartphone and handheld device. If the authentication fails, then the wellness and wellbeing information system will terminate the Bluetooth pairing in Auth (step 707) before any user data or communication through the Bluetooth connection commences. Since self-authentication is required whenever the application interface (App) is launched (step 701) state by the user, if either the smartphone or the wellness and wellbeing information system or both are lost or stollen then the authentication process (700) will prevent unauthorized user to access the wellness and wellbeing personal data stored in the wellness and wellbeing information system.

Particular embodiments of a wellness and wellbeing information system are configured to allow the user to adapt the system to the user's scope of ambient monitoring needs. In particular embodiments, a user has two options for range of user ambient monitoring: (1) immediate ambient area surrounding the wellness and wellbeing information system that is used as a protective case or sleeve for smartphones and handheld devices provides a fully integrated ambient monitoring around the user; and (2) user defined extended monitoring area of indoor-space using one or more range extender remote ambient pollution monitoring subsystems (see FIG. 6 and related description) that form a wired network through powerline Ethernet communication. The range extender ambient pollution monitoring subsystems are configured to plug into the AC wall power outlets of a house, a facility, or a building to provide continuous ambient monitoring in communicative cooperation with the user's individual wellness and wellbeing information system. The user receives status information of pollution condition from the entire monitored indoor-space through the wellness and wellbeing information system where it connects to only the nearest range extender remote ambient monitor to receive the pollution condition data collected from the entire network of remote ambient pollution monitors.

The range extender remote ambient monitoring subsystems are configured to provide audiovisual alarms indicating the severities of the detected concentration of the ambient pollutions that exceed the user defined thresholds at their respective monitored indoor locations. The remote ambient pollution monitoring subsystems keep any collected data locally and will only send to synchronize with the wellness and wellbeing information system when the designated active remote ambient pollution monitor establishes a Bluetooth connection to the wellness and wellbeing information system fitted with the users' smartphone or handheld devices. This arrangement between the embodiment of the wellness and wellbeing information system and the range extender remote ambient monitoring systems eliminates the need for continuous transmissions of wireless Bluetooth signals from all the remote monitors that would contribute to the radiofrequency ambient radiation pollution in the indoor-space. Furthermore, the remote ambient monitoring subsystems provide the added benefit of creating a wired network access points that are available throughout the user defined monitored indoor-space. This will enable the users to mitigate the inherent risk of exposure to the RF signal radiation pollution from the indoors' WiFi networks that is common in the indoor-space but contribute to a significant amount of radiofrequency signal radiation pollution in the indoor-space.

Exposure to airborne pollutants like CO and $NO_2$ gases directly pose risk to the wellness and wellbeing of the users. Although smoke and certain gas detectors are commonly found in the indoor-space the users are not typically able to set their desired threshold limits to be monitored and to receive the potential impact to their wellness and wellbeing for experiencing exposure to CO or NO2. Similarly, other indoor pollutants in the ambient of the user that include but not limited to VOC, particulate matter (PM), dust, allergens, etc., have potential adverse effects to user's wellness and wellbeing. Particular embodiments of a wellness and wellbeing information system may be configured to track the user's ambient airborne pollution and contextualizes any impact to the user's wellness and wellbeing. For example, the embodiment assesses any effect to the autonomous nervous system (ANS) that could induce a temporal condition to the dynamic state of the ANS that leads to changes to blood pressure (BP) and heart rate variability (HRV) and other biomarkers. Users will receive personalized information of the cause and effect of exposures to, for example, elevated concentrations of VOC, or Particulate Matter (PM), or indoor allergens among other pollutants that could have direct effect to the user's heart rate variability (HRV) and other biomarkers.

Particular embodiments of a wellness and wellbeing information system of the present disclosure culminates various global environmental safety guidelines and adopts the most risk averse recommendations as a default setting for staying on vigilant about the risk of ambient pollution exposure in the indoor-space. Systems may be configured to derive the default threshold limits from the guidelines and recommendations of BioInitiative and Building Biology Institute (BBI) that focus on biological adverse effects of the ambient pollution concentration to people's wellness and wellbeing. Particular embodiments will guide the users to either accept and confirm the suggested default settings or modify them to any desired settings for personalized ambient pollution threshold limits. This functionality enables personal environmental quality monitoring for people who are more sensitive to various ambient pollution conditions caused by poor air-quality, gases, volatile organic compounds, allergens, dust mites, pollens, mold spores, particulate matter PM2.5 and PM10, temperature variations, high or low relative humidity, magnetic field strength, electric field strength and radiofrequency signal radiation to adapt to their specific and suitable conditions.

An embodiment of the present disclosure enables personalization of user defined wellness and wellbeing objectives that become threshold parameters that all analyzes are based on. It provides a contextualized user specific information about the current status and progress of the user's deliberate effort toward short- and long-term objectives. Users with underlying condition will be able to customize the context of their personal data and the baseline of their biomarker data that get incorporated into their wellness and wellbeing objectives. For example, a user who has asthma or high blood pressure or heart condition or other conditions will be able to personalize to receive contextualized information that is specific to their needs. The system raises the awareness and vested interest of the users to wellness and wellbeing, and to guide the user's deliberate efforts in achieving an individualized wellness and wellbeing objective.

A particular embodiment of a wellness and wellbeing information system used as protective case for smartphones and handheld devices includes integrated subsystems for ambient sensors and physiological biosensors to collect and co-analyze comprehensive data for the user's ambient pollution condition and user's physiological biomarkers condition. In such an embodiment, the system will increase the value and the utility realizable from holding a smartphone and a handheld device in the hands of the users excluding hands that are covered with gloves or similar covering, and when the devises are kept close by the user. Since smartphones are in use significant part of the day, they are held in the hands of the users while they are in use, and they are kept within hands' reach when they are not in use.

Particular embodiments of a wellness and wellbeing information system continuously aggregates and co-analyzes users' ambient pollution conditions and physiological biomarker conditions without requiring separate devices to collect ambient pollution data and another device for wellness related data that is to be worn on the users' body.

Particular embodiments also provide protection for accidental drops of the smartphones and handheld devices in an ergonomically suitable means to hold these devices with either one hand or both hands in portrait and in landscape orientations. Such a system also aligns the contacts between the palm and fingers of the user's hands with integrated biosensors which requires no more effort than holding naturally the fitted smartphone and handheld devices. Once the personal wellness and wellbeing monitoring is configured with personalized objectives that derive the thresholds of varies monitored ambient conditions and biomarker conditions, the particular embodiments described FIGS. 2-4 and FIG. 6 autonomously collect data, process the data and updates the user interface (App) provided that the user is authenticated in passive mode (11 FIG. 1A). For example, the personal wellness and wellbeing monitoring system will continue to collect ambient pollution and physiological biomarker data after it is configured and authenticated in passive mode even if the user shuts down the user interface (App), or shuts down the smartphone and handheld device, or the smartphone and the handheld device run out of battery. The user will get information update upon relaunching the user interface (App) and re-authenticating successfully.

Figure 1B:
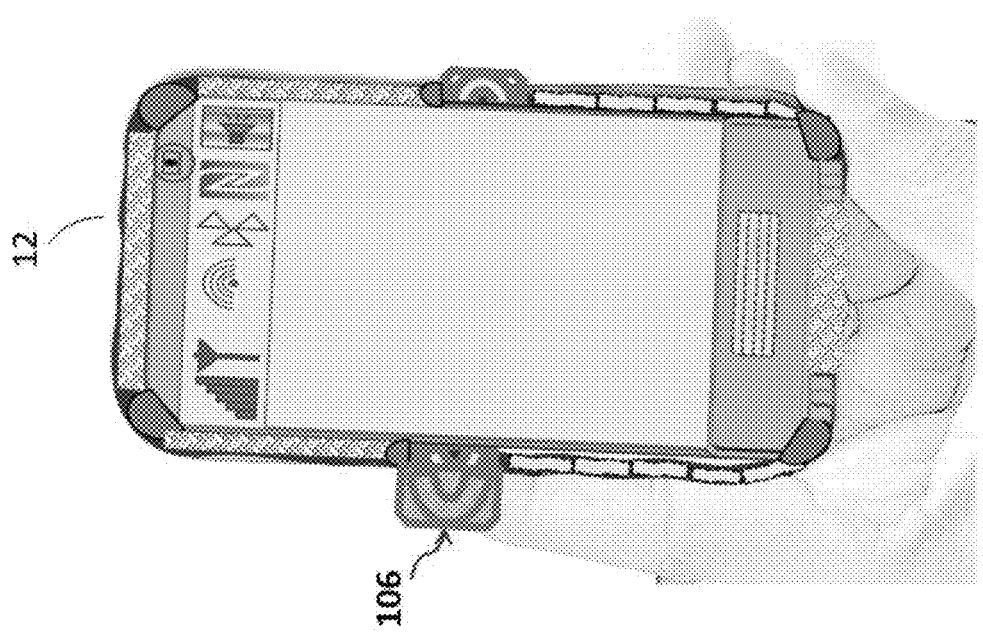
Figure 1C:
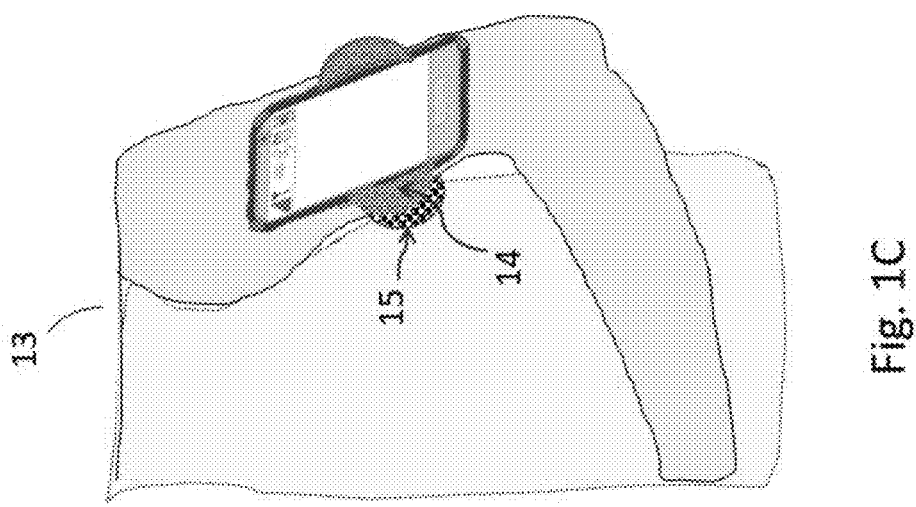

The wellness and wellbeing information system functions in three modes of operations: interactive (12 FIG. 1A), passive (11 FIG. 1B), and physical (13 FIG. 1C). In passive mode, the embodiment (11 FIG. 1A) collects, processes, and contextualizes ambient data and physiological data periodically while fitted with a smartphone and handheld device throughout the day. At each cycle, the embodiment collects ambient pollution data and also senses any contact between the users' hand-palms and fingers to the biosensor front-ends. And if any contact is detected and verified where the user's hand-palm is in contact with the integrated sensors then user's physiological biomarker data is collected without the user being aware of it or require getting involved in the data collection process. The embodiment updates continuously user specific contextual information that is readily available to the users and sends alerts if there are any potential adverse condition to the user's wellness and wellbeing. The users can change periodicity of the passive mode data collection to suite their wellness and wellbeing objective.

In interactive mode, the user explicitly initiates the collection of the physiological biomarkers data and ambient pollution condition data through menu options in the user application interface (App). The embodiment (12 FIG. 1B) requires the user to insert either a right-hand or a left-hand finger into an elasticated and secured biosensor fitting (106 FIG. 2A) located on either side of the universal holder before initiating physiological biomarker data collection. Similarly, the embodiment requires the user to select either an indoor or outdoor for ambient type through a menu option to initiate the interactive mode ambient pollution data collection. The users have complete control of when to initiate the data collection and to receive a contextualized and a personalized information about their wellness and wellbeing.

In physical mode, the embodiment (13 FIG. 1C) of the wellness and wellbeing information system may be configured to require the user to explicitly initiate through the App's menu option to start a continuous collection of the physiological biomarker data after successfully validating the extension strap (14 FIG. 1C) integrated with biosensors (15 FIG. 1C) is attached of to the universal holder. The strap extends the universal holder's use-cases where the users can flexibly use it for various aspects of their daily routines like physical exercise or physical monitoring. For example, data collection from user's underarm by aligning it with the brachial artery when the strap that is attached to the wellness and wellbeing information system is worn on the upper arm during physical exercise like jogging in outdoors or working out in an indoors gym. The strap can be worn on any part of the arms or the legs, and the wellness and wellbeing system guides the users to properly align the desired contact points between an artery and biosensors section (15 FIG. 1C) of the extension strap (14 FIG. 1C) as part of the process of initiating the physical mode through a menu option of the user interface application (App). The embodiment using the physical mode could also provide status updates to a prearranged and authorized third-party about the status of the users like lone-worker or elderly person who lives alone.

Figure 2C:
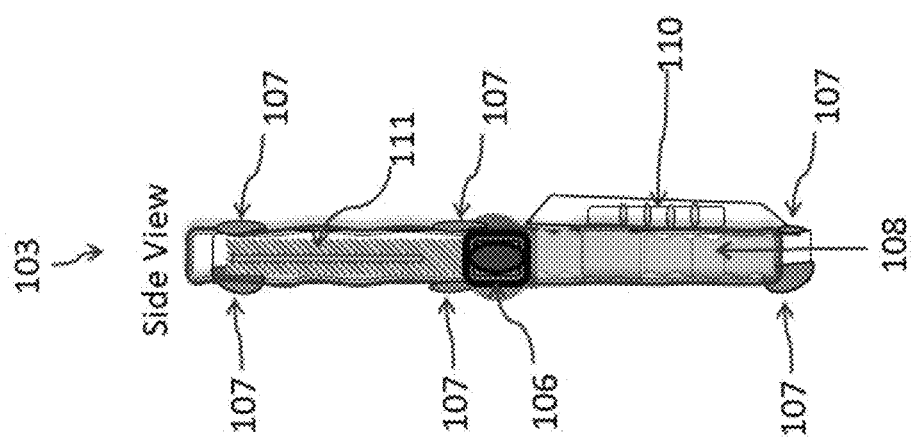
Figure 2D:
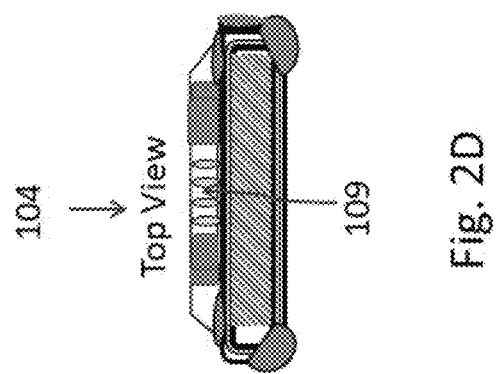
Figure 2E:
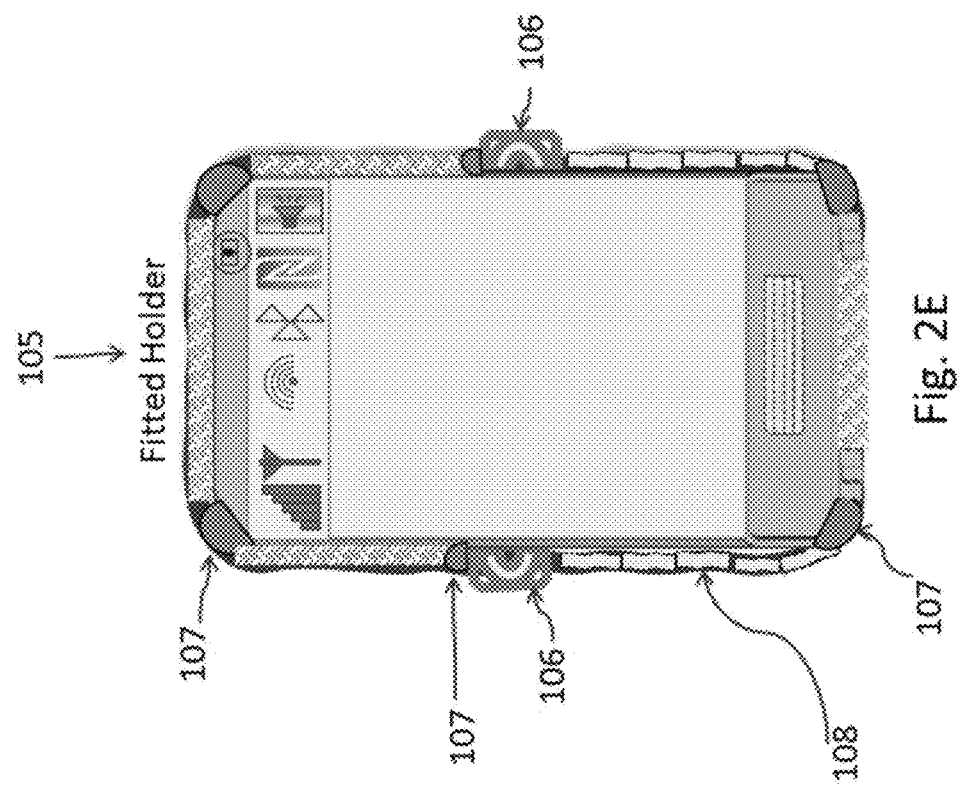
Figure 3C:
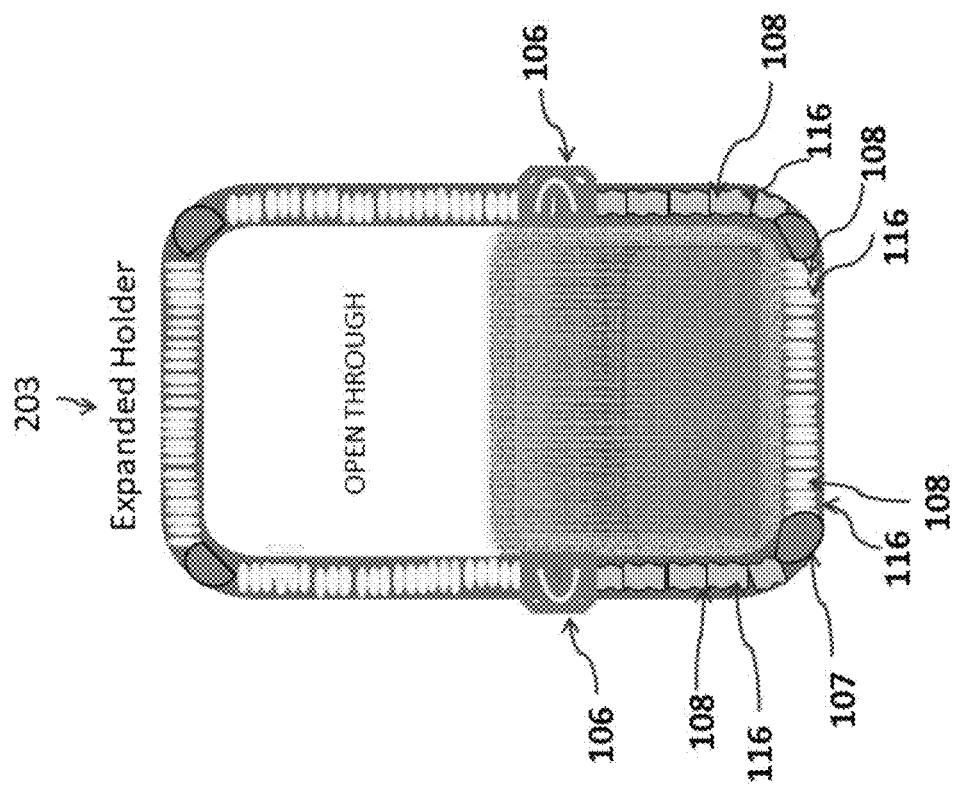
Figure 4B:
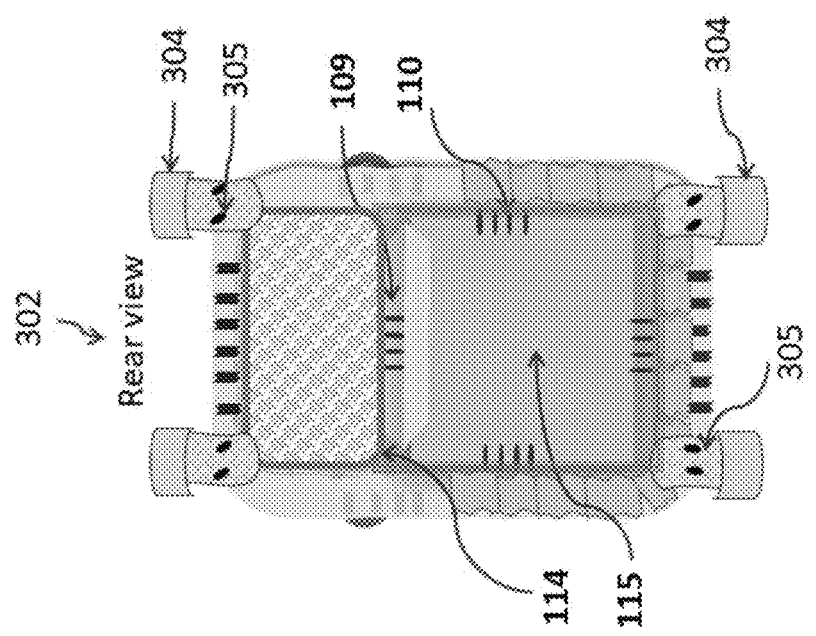
Figure 4C:
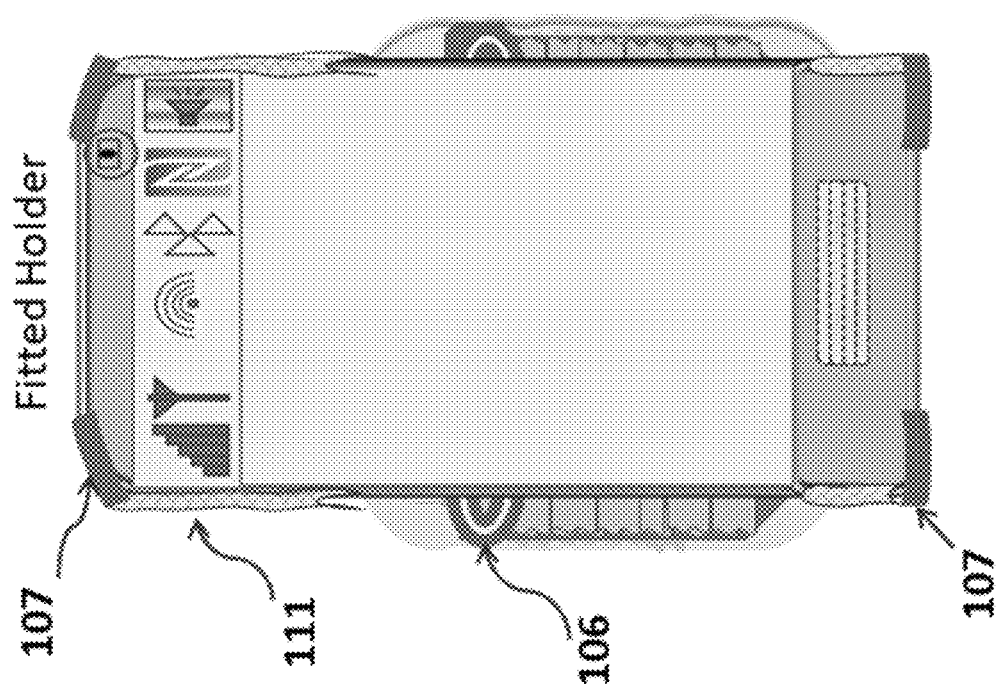

FIGS. 2A-4C illustrate three different protective holder configurations for a wellness and wellbeing information system. FIGS. 2A-2E illustrate a wellness and wellbeing information system integrated into a protective case configuration that stretches both vertical and horizontal dimensions. FIGS. 3A-3C illustrates a wellness and wellbeing information system integrated into a protective case configuration that expands through the addition of links to fit any desired sized smartphones and handheld devices. FIGS. 4A-4C illustrates a wellness and wellbeing information system integrated into a protective sleeve configuration with four arms (304 FIG. 4A) that stretch vertically to the corners of the smartphones and handheld devices to fit various devices.

The wellness and wellbeing information system shown in FIGS. 2A-2E illustrate the wellness and wellbeing information system integrated in a protective case for smartphones and handheld devices showing front view (101 FIG. 2A), rear view (102 FIG. 2B), side view (103 FIG. 2C) top view (104 FIG. 2D) and fitted with a smartphone (105 FIG. 2E). The embodiment of the wellness and wellbeing information system integrated in the protective case has the top half of the case open through and it has no back cover which practically exposes the rear side of smartphones that typically have cameras and flashlight while facilitating the smartphones' capability for wireless charging. FIG. 2A illustrates three functional adjustable sections (112), (113) and (114) to adapt to the desired size and dimensions of smartphones and handheld devices. The embodiment expands horizontally using elasticated sections (112 FIG. 2A) of the top and bottom rim to enlarge the case, expands vertically using elasticated sections (113 FIG. 2A) in the left and right sides to elongate the case. Elasticated frame (114 FIG. 2A) around the fixed section (115 FIG. 2A) facilitates the expansion of the case to adapt different sizes of smartphone and handheld devices. The wellness and wellbeing information system uses fixed and ruggedized section (115 FIG. 2A) to house the core electronics that has shock and impact absorbents to protect components.

The particular embodiment illustrated in FIG. 2A has a key feature of integrated biosensor in elasticated and secured single finger fitting (106 FIG. 2A) on both sides of the wellness and wellbeing information system where users' finger can be inserted in either side (106 FIG. 2A)—on the left side for a left-hand finger or the right side for a right-hand finger. FIG. 2A illustrates another key feature of front-end biosensors (108 FIG. 2A) and front-end ambient sensors (116 FIG. 2A) respectively that are integrated in multiple location when fitted with a mobile device like smartphone that ergonomically positions contacts between the wellness and wellbeing information system and the user's hand-palm and fingers where the user will typically grip to hold on the fitted with smartphone and handheld device. FIG. 2C illustrates transparent and reach-through sections (111 FIG. 2C) that enables the users to access any control interfaces on the perimeter of the devices fitted in any of the illustrated embodiments. FIG. 2C conveniently illustrates impact absorbents (107 FIG. 2C) in the front and the back of the protective case that also maintain a clearance between the fitted smartphone and any plain surface. FIG. 2C illustrates the key features of horizontal inlet/outlet ambient air sample vents (110 FIG. 2C) with respect to the fitted mobile device, and FIG. 2D illustrates vertical inlet/outlet ambient air sample vents (109 FIG. 2D) with respect to the fitted mobile device.

FIGS. 3A-3C illustrates an embodiment of a wellness and wellbeing information system integrated into a protective case configuration that expands through the addition of links to fit any desired sized smartphones and handheld devices. FIG. 3A shows (201) front view of the case and the extension links (204 FIG. 3A) that facilitate the adaptation of the case into the desired size. FIG. 3B shows (202) back side view and FIG. 3C shows (203) a case fitted to the desired size smartphone.

FIGS. 4A-4C illustrate an embodiment of a wellness and wellbeing information system integrated into a protective sleeve. FIG. 4A shows the front view (301) of the sleeve, four arms (304 FIG. 4A) that stretch to reach the four corners of the device that is unfolded if such a device could fold to fit any desired sized smartphones and handheld devices. FIG. 4B show (302) the rear view, elasticated impact absorbents (305 FIG. 4B) that are integrated at multiple point on the four extending arms (304 FIG. 4B).

Figure 5:
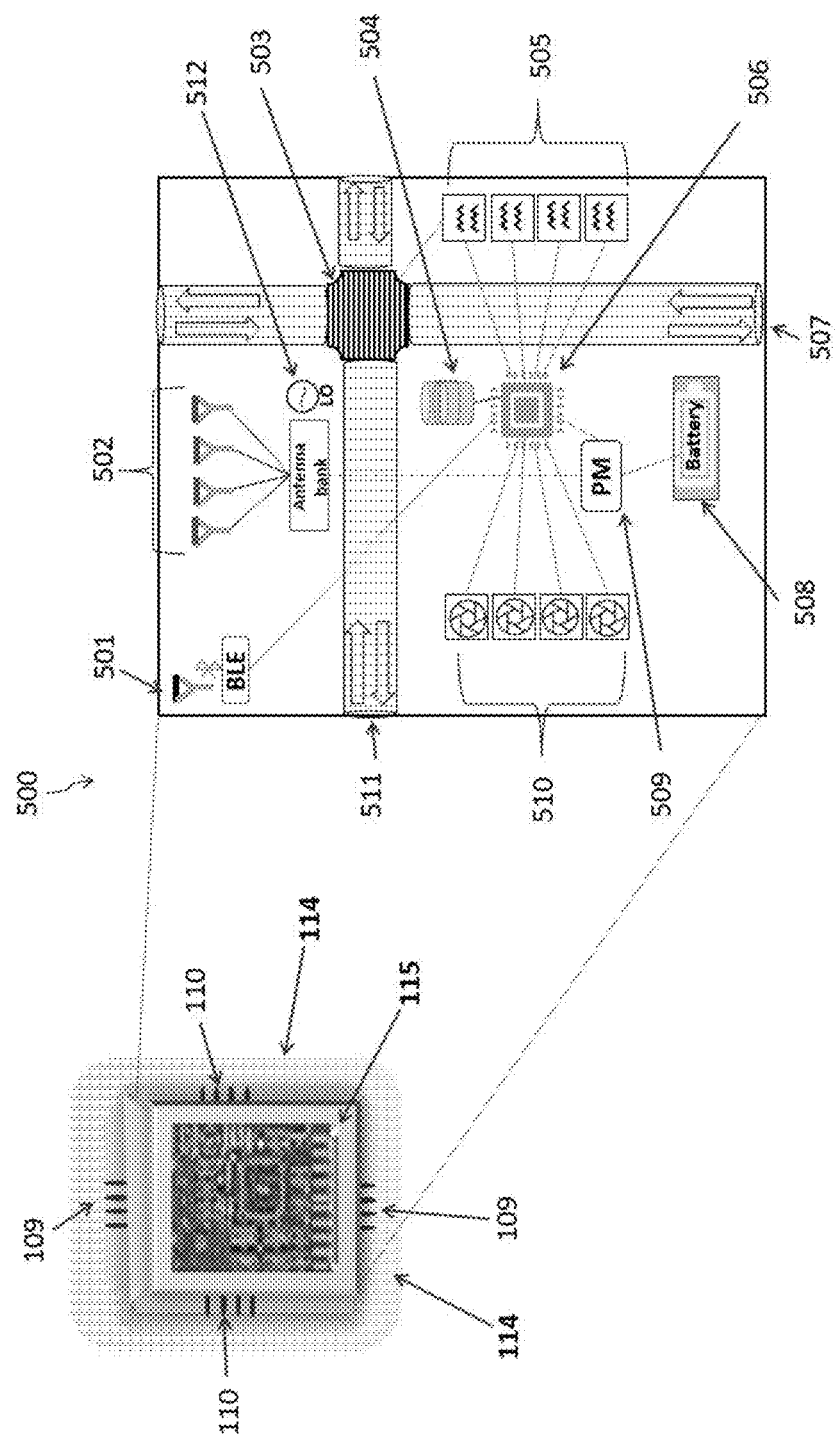
FIG. 5 illustrates a core system for processing ambient pollution and physiological biomarkers in a wellness and wellbeing information system.

FIG. 5 illustrates the core electronics (500) of the wellness and wellbeing information system shown in FIGS. 1-4 and includes a Bluetooth low energy with dedicated antenna (501), and ambient pollution subsystem that has a bank of antennas (502) to simultaneously scan on different frequencies between 1 Hz to 300 GHz using (512) either dedicated or tunable local oscillator (LO) to search and tune to any electric field, magnetic field, and RF signal radiation pollution. The ambient pollution subsystem also has a bank of sensors (505) with different functionalities to collect data from multiple front-ends sensors (116) (FIG. 2A), for various ambient data including air-quality, gases, volatile organic compounds, allergens, dust mites, pollens, mold spores, particulate matter with diameter less than 2.5 and 10 micrometer, temperature, and relative humidity. The particle matter sensors are capable to detect 1 to 10 micrometers. A second bank of biosensors (510) with different functionalities collects biomarker data from multiple sensor front-ends (108 FIG. 2A) integrated in the wellness and wellbeing information system's ergonomically guided gripping positions where a user will hold on to the protective case or sleeve that is fitted with the smartphone and handheld devices.

Embodiments of a wellness and wellbeing information system inform the users the ambient radiation pollution exposure levels and the risk of potential adverse effects to the users' defined wellness and wellbeing objectives. As the use of 20 GHz spectrum and higher for faster consumer data communication increases, the implication of their exposure to the wellness and wellbeing of the users is of a great concern because BioInitiative documents many research that have shown the centimeter-wavelength spectrum that was in use for the past decades causes biological cell stress at levels that are magnitude lower than the regulatory SAR limits without the users experiencing any perceivable thermal effect. Since exposure to radiation pollution is ever-growing phenomena, the risk of the cumulative biological adverse effects that this could stimulate to a user's wellness and wellbeing potentially increases. A wellness and wellbeing information system enables users to be continuously informed about their experience to electric field, magnetic field and RF signal radiation exposure and their cumulative potential effect to the monitored physiological biomarkers.

Particular embodiments illustrated detect the orientation of the wellness and wellbeing information system fitted with smartphone and handheld device to maintain a controlled top-down airflow mechanism to analyze the ambient airborne pollution condition using first and second vents (507) and (511). For example, when the user is holding the smartphone in portrait or vertical orientation then the wellness and wellbeing information system uses a first vent (507) to draw external air sample from top facing side vents (109 FIG. 2D) to pass it through optical particle sensor chamber (503) before guiding the air out through the opposite passage (507) to bottom vents (109 FIG. 2D). Similarly, when the user is holding the smartphone that is fitted with the wellness and wellbeing information system in landscape or horizontal orientation then the external air is drown from top facing second vents (511) and corresponding passage into the optical particle sensor chamber (503) before directing the air to exit through the corresponding bottom vents (110 FIG. 2C). This top-down airflow mechanism ensures that the sampling air is always drawn into the wellness and wellbeing information system from typically unobstructed top side that is exposed to the users' ambient without requiring any user involvement.

The embodiment of the wellness and wellbeing information system has a self-contained processor (506) that could be configured as a system-on-chip, or other configuration known in the art, which collects and processes the ambient pollution and physiological biomarker data from respective sensory subsystems. The processor (506) is configured as a processing function for ambient pollution and physiological biomarker data, and to store both raw and postprocessed data into (504) secure internal non-volatile storage. The processor (506) updates the user application interface (App) and it maintains the rolling hysteresis of ambient pollution condition and physiological biomarker condition data to analyze current trend and to forecast expected outcome of the user's target wellness and wellbeing objectives. For example, a user's actual exposure experience to ambient pollutions like average and peak concentrations of PM2.5, VOC, RF radiation, and so on during the first 12 hours of the day could be used as a predictor data to forecast the possibly of exceeding the user's defined daily exposure limits. This could generate an alert that warns the user any potential allergic or other potential adverse effects to heart rate variability (HRV) and user's baseline wellness and wellbeing condition. Hysteresis data (953 FIG. 9) is also used to co-analyze the physiological biomarker conditions and trends of ambient pollution conditions. In the example of exceeding ambient pollution exposure for VOC or PM2.5, the user who set to maintain certain average blood pressure during the day could get an alert for adverse effect of the wellness and wellbeing.

Embodiments of the wellness and wellbeing information system used as a protective case or sleeve for smartphones and handheld devices has a rechargeable battery (508) that is charged from AC power when the battery needs a charge. During the normal operation of the wellness and wellbeing information system its battery (508) takes advantage of two other possible source of charging. First, the battery (508) could be recharged through a wireless charging while the users are charging their smartphone and handheld device that is fitted with the universal holder. Second, the battery (508) could be recharged by efficiently recycling any detected ambient radiation pollution from magnetic field strength, electric field strength and the RF signal by converting them to DC using charge controller and power management module (509). Whenever the wellness and wellbeing information system detects any electromagnetic radiations pollution regardless of whether an alert was raised or not for potential risk to the users' wellness and wellbeing, the effected users will get some extra battery life that will serve them for continued longer monitoring of their ambient pollution.

The embodiments of the wellness and wellbeing information system used as a protective case or sleeve for smartphone and handheld device may additionally use an attachment (13 FIG. 1C) to affix the wellness and wellbeing information system on the users' arm or leg. The strap (14 FIG. 1C) enables the user, for example, to wear the wellness and wellbeing information system on the upper arm securely and comfortably when using the wellness and wellbeing information system in physical mode. The strap (14 FIG. 1C) has integrated biosensors section (15 FIG. 1C) that requires to be aligned with brachial artery in the under-arm to collect biomarker data during physical exercise activities. The users could also wear the strap (14) on any part of the arm or the leg, and the wellness and wellbeing information system's user interface application (App) will guide the users until the (15 FIG. 1C) biosensor section aligns with an artery in the arm or the leg to commence the collection of the biomarker data in the physical mode.

Particular embodiments may be configured to detect and track concentrations of pollutants like PM2.5, PM10 and VOC, directly emitted gases and other gases formed through chemical reaction that have potential to pose risks to the users' wellness and wellbeing. For example, exposure to elevated VOC concentrations and other allergens lead to allergic rhinitis reaction that could impact the HRV and potentially affect the general cardiovascular condition. Another example, the embodiment alerts immediately the users even short-term exposure to elevated concentrations of fine particles of less than 2.5 μm (PM2.5) because they could set off pulmonary nerve reflexes that activate and cause imbalance to the autonomic nervous system (ANS) which results alterations of heart rate variability (HRV), increased diastolic blood pressure (BP) and induce other physiological conditions like arrhythmias that increase overtime risk of cardiomyopathy. Another example, the embodiment alerts the users exposure to humidity level that is higher or lower than the user defined threshold limits. This will guard against the exposure to higher relative humidity that could cause both dust mite populations and mold colonies to grow, and it will greatly increase total allergen load exposed to those who are suffering from allergy.

Figure 6:
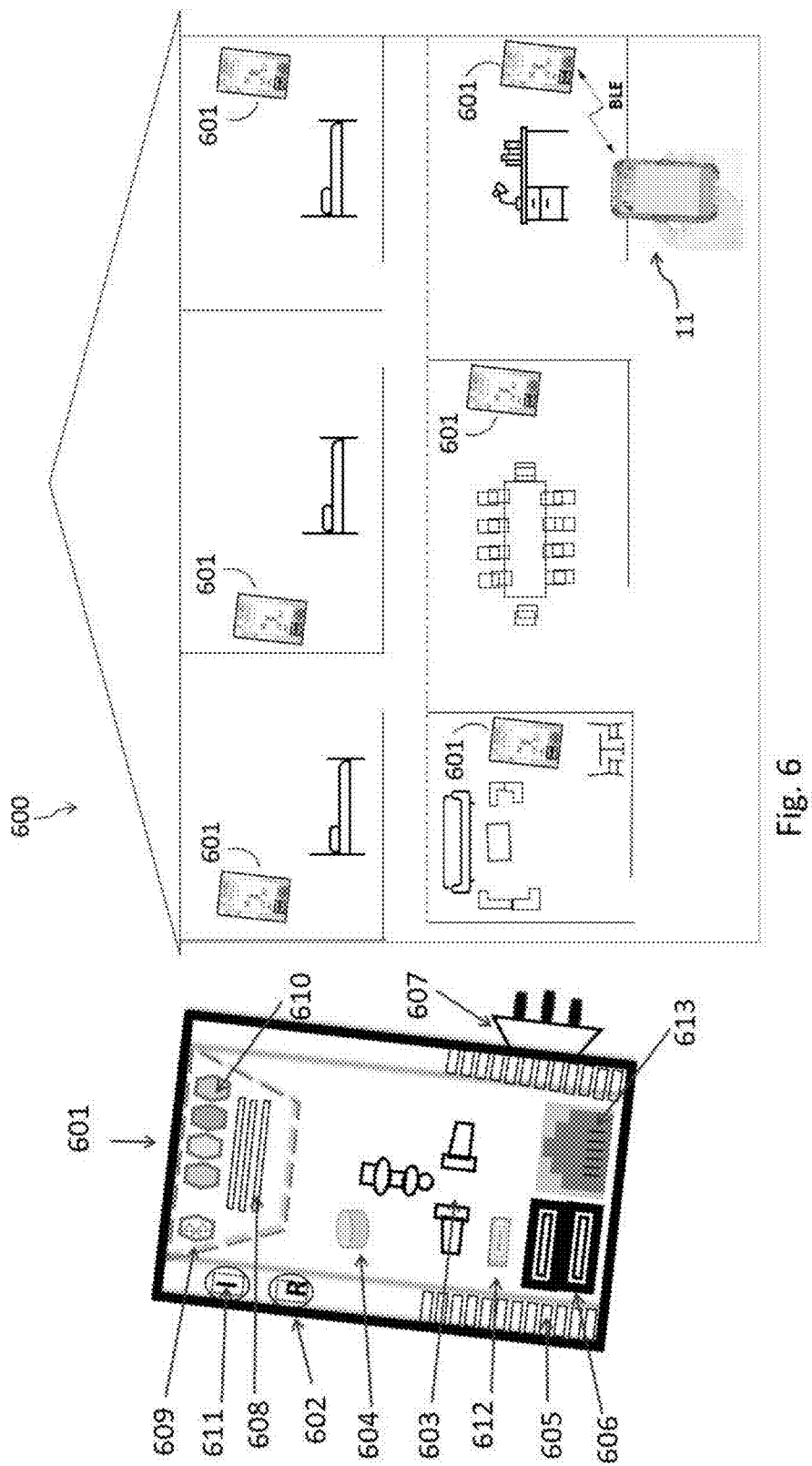
FIG. 6 depicts an embodiment of range extended remote ambient pollution data collection.

Embodiments of a wellness and wellbeing information system may also be configured to use a range extender subsystem for remote ambient pollution data collection (601) to extend the monitored indoor-space enabling the users to continuously receive updates of the ambient pollution condition of the desired indoor-space like multi-room, multistory house, or large facility. FIG. 6 illustrates an embodiment of a wellness and wellbeing information system (601) with an electrical cord (607) configured to plug into plugs for AC power, and it has power on/off switch (611), reset switch (602), standard AC interface socket (603), standard USB interface (606), standard RJ-45 port (613), Bluetooth pairing indicator (609) when connected to the wellness and wellbeing information system for data synchronization. Visual alarm status indicator LEDs (610), audio alarm to alert the user (608), airflow vents in/out for analyzing ambient airborne (605) pollution, non-volatile memory for data storage (604) and standby battery (612) are also included and interfaced with the processor (506). The wellness and wellbeing information system's range extender remote ambient pollution monitor may be configured to operate with AC power that it also uses as the medium to establish wired networking access through Ethernet over power line standard. The remote ambient pollution monitors send their respective data primarily via the Ethernet over powerline except the active remote ambient pollution monitoring unit that has Bluetooth paired connection due to its proximity to the universal holder. Only the closest remote ambient pollution monitoring unit to the wellness and wellbeing information system establishes a Bluetooth connection to synchronize the data collected from the entire wired network of distributed remote ambient pollution monitors with a wellness and wellbeing information system.

The range extender remote ambient pollution monitoring system embodiment of the wellness and wellbeing information system (601) provides the users an alternative method for wired Internet access within the entire monitored indoor-space. For example, using a RJ45 Ethernet cable to a close by wellness and wellbeing information system (601), the users will be able to mitigate the inherent risk of using WiFi wireless Internet access in the indoor-space that generate radiofrequency signal radiation pollution and a long-term exposure that has potential adverse effect to the users' wellness and wellbeing objectives. As another example, the range extender remote ambient pollution monitoring subsystem could become part of the home network where the users will be able to receive the ambient pollution condition status while they are away from their homes. Hence, knowing an elevated PM concentration or increased relative humidity before a user walks into an indoor-space will facilitate the planning and the immediate steps that the user could take to mitigate the ambient pollution exposure risk like opening the windows to air the indoor-space or to turn on if the user has an air filtration system upon returning to the indoor-space. Users can implement proactive approach to mitigate exposure risks to potentially harmful indoor-space pollution concentration.

Figure 8:
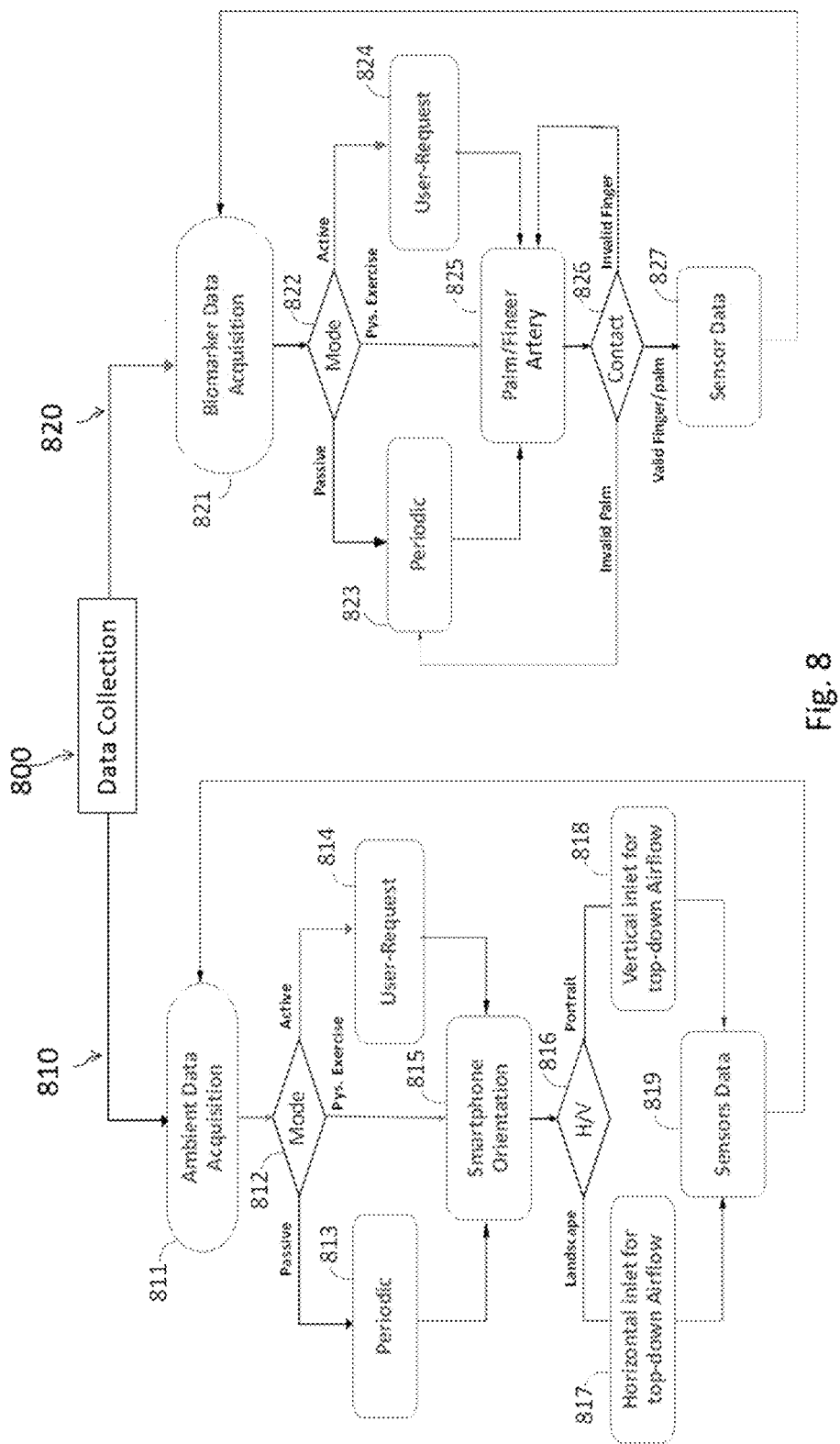
FIG. 8 illustrates the system's process for collecting ambient data and biomarker data.

In relation to FIG. 8, the data collection process (800) that has a parallel paths for data acquisition from ambient pollution (810) and physiological biomarker (820) covering interactive mode, passive mode, and the physical mode. The data collection process (800) along the path (path 810) initiates the Ambient Data Acquisition (step 811) that immediately checks the Mode (step 812) of system operation. If the system is operating in passive mode, then it obeys the preset Periodic (step 813) cycle before checking the Smartphone Orientation (step 815). If the system is operating in interactive mode, then it takes the user-initiated User-Request (step 814) the type of ambient selected by the user through the App interface before checking the Smartphone Orientation (step 815). If the system is operating in physical mode, then it immediately checks the Smartphone Orientation (step 815). Depending on the smartphone orientation, landscape orientation will user Horizontal Inlets for Top-Down Air Flow (step 817) and portrait orientation will user Vertical Inlets for Top-Down Air Flow (step 818). The process collects data for ambient pollution condition from ambient Sensors Data (step 819) and cycles back to (step 811) state.

The data collection process (800) along the path (path 820) initiates the Biomarker Data Acquisition (step 821) that immediately checks the Mode (step 822) of system operation. If the system is operating in passive mode, then it obeys the preset Periodic (step 823) cycle before detecting the user's palm in Palm (step 825). If the system is operating in interactive mode, then it takes the user-initiated User-Request (step 824) to immediately detect a finger is inserted in any of the two single elasticated finger secured biosensor fitting in Figure (step 825). If the system is operating in physical mode, then it immediately detects an artery in the limp the biosensor extension strap in worn in Artery (step 825). Depending on the outcome of the Detection (step 826), a valid contact detection leads to acquisition of Sensor Data (step 827) and loop back to (step 820), an invalid contact detection loops back to wait next Periodic (step 823) or finger detection (step 825).

For example, the interactive mode requires the user to select either ambient pollution condition or physiological biomarker condition from the user application interface (App) for an immediate status query. If the user selects the ambient pollution condition then the application interface (App) will further prompt the user to select and identify the type of environment as either indoors or outdoors. The user's request will lead to data acquisition from the type of ambient selected and a contextual snapshot of the ambient pollution condition and user's wellness and wellbeing. But if the user selects the physiological biomarker condition then the system will first check whether the user has inserted a finger into one of the single finger elasticated and secured biosensor fittings (106 FIG. 1A) on either side of the wellness and wellbeing information system that is used as a protective case or sleeve for smartphones and handheld devices. The wellness and wellbeing information system will not initiate until a validated finger is inserted into either of the single finger secured biosensor fittings because the user's interactive mode request is for a controlled physiological biomarker data collection of the rightful owner of the wellness and wellbeing information system that also avoids tampering and biasing the hysteresis data from the owner's physiological biomarkers.

The user validation is especially important because the rightful owner of the wellness and wellbeing information system could possibly let a friend or a family member to try to use the single finger elasticated and secured biosensor fitting and make a request though the user-interface application (App) to get a status. Since the data collected from the single finger secured biosensor fitting is treated as a controlled data, it is an integral part of the continuous user specific baseline calibration data to train the user's baseline data. Successful initiation of the interactive mode request will lead to simultaneous data acquisition from the environmental sensors and physiological biosensors from both validated single finger that is inserted in secured biosensor fitting (106 FIG. 1A) and any other detected contact between user's hand palms and fingers, and (108 FIG. 1A) front-end biosensors that passively collect biomarker data. The collected active data set is aggregated and co-analyzed to provide a contextual status snapshot of a user specific wellness and wellbeing information.

The embodiment in passive mode will collect periodically using the ambient pollution condition data (116 FIG. 1A) and will simultaneously detect through biosensors (108 FIG. 1A) any valid contact from the users' hand palm and fingers to start collecting physiological biomarker data for the current periodic cycle. The passive mode data collection for both ambient pollution condition and physiological biomarker condition require no direct user involvement or even awareness after uses set their desired periodic cycle like every 5 minutes or any time interval that the individual user chooses to set through the user-interface application (App). The outcome of the data analysis will update the status information that is always available to the users through the App and suggests possible remedy to rectify any indoor pollution condition.

A key feature of the wellness and wellbeing information system used as a protective case or sleeve for smartphones and handheld devices is utilizing the users' natural way of gripping their smartphones and handheld devices to hold them. This provides opportunities to detect any valid contacts between the users' hand palms and fingers, and biosensor front-ends (108) that collect physiological biomarkers data. Therefore, the passive mode is a candid process that is intended to collect unbiased data throughout the day that will reflect on the users' daily cycles of wellness and wellbeing condition.

A wellness and wellbeing information system in the physical mode will provide a mechanism for the super-active, physically-active and physically inactive users a suitable means for their wellness and wellbeing data collection, respectively. Super-active and physically-active users will be able to use their wellness and wellbeing information system fitted as protective case or sleeve to their smartphones during their physical activities where the wellness and wellbeing information system will incorporate continuously gathered data to the contextualization of the users' progress toward their wellness and wellbeing objectives. Physically inactive users that includes elderly people could have their personal wellness and wellbeing data calleted continuously or at any desired rate in the wellness and wellbeing information system.

FIG. 1C illustrates a wellness and wellbeing information system configured with a strap (14 FIG. 1C) that holds it to any part of the users' arms or legs. FIG. 1C illustrates the strap (14 FIG. 1C) attached to the wellness and wellbeing information system to keep the fitted smartphone on the upper arm where a specially positioned biosensor section (15 FIG. 1C) detects the alignment with the brachial artery in the upper arm to continuously collect biomarker data. During activation of the physical mode through the user interface application (App), the biosensor section (15 FIG. 1C) of the extension strap (14 FIG. 1C) will detect arteries in the arms or in the legs depending on where the strap (14 FIG. 1C) is securely attached on the user's arm or leg. The physical mode continuously collects physiological biomarker data, ambient pollution condition data and various other sensory data that include rate of displacement and body temperature until the user deactivates or simply removes the strap from the user's body contact in which case the user-interface application (App) will immediately deactivate and produce contextualized information.

Figure 9:
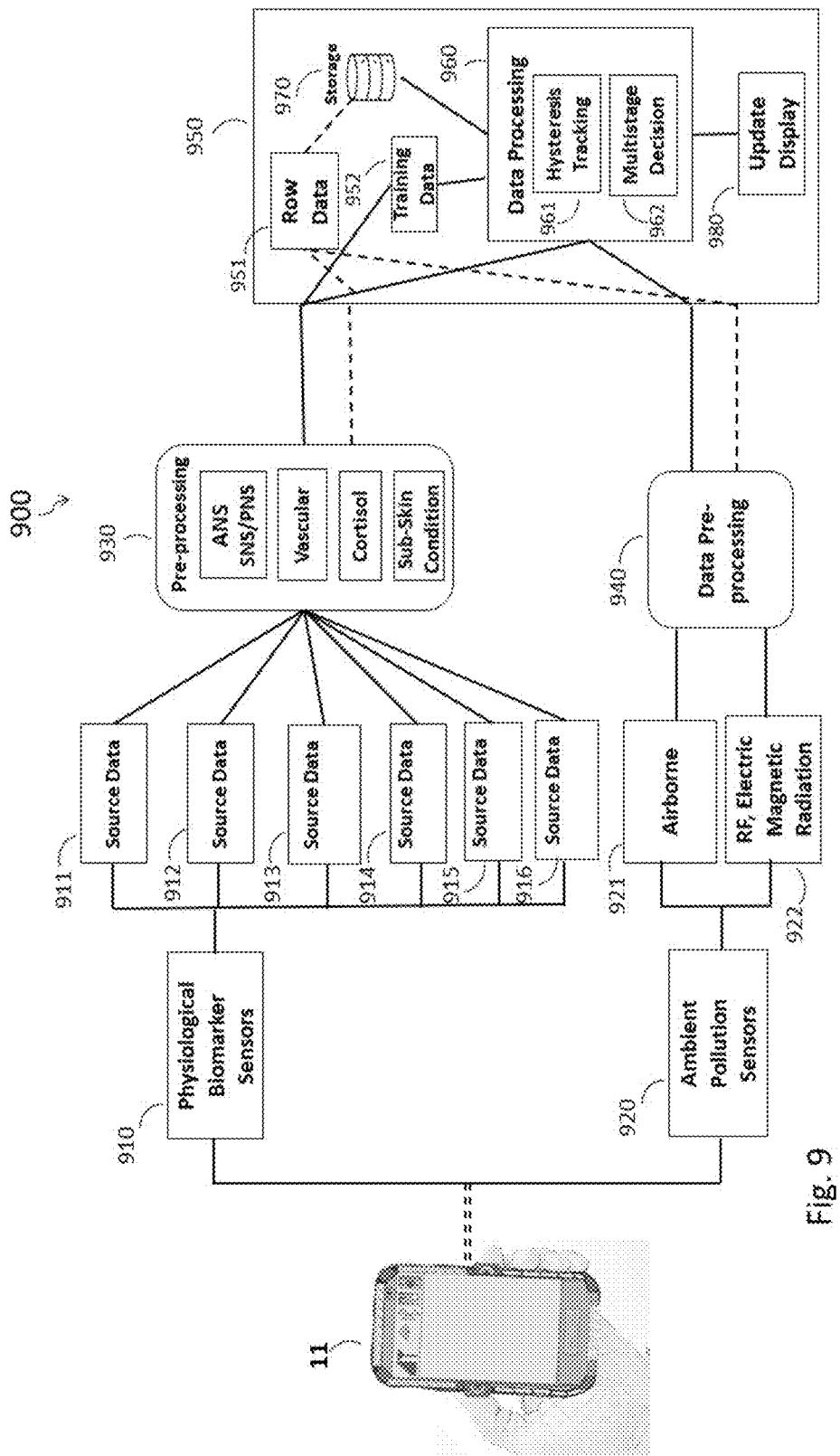
FIG. 9 illustrates the system's process for contextualizing user's wellness and wellbeing condition.

FIG. 9 illustrates the wellness and wellbeing information system integrated with physiological biomarker sensors (910) and ambient pollution sensors (920). The physiological biomarker sensors (910) are configured to use electrocardiography (ECG) biosensor (911) for measuring electrical signals that control the expansion and contraction of the heart chambers, photoplethysmography (PPG) biosensor (912) for measuring the rate of the blood flow pumped out of the heart, electrodermal activity (EDA) biosensor (913) for measuring Galvanic Skin Conductance (GSR) of the sweat gland activity as a result of arousal, Cutaneous Micro Circulation (CMC) biosensor (914) for measuring skin temperature at different depth levels, Pulse Oximeter (915) for measuring oxygen saturation, and fingernail Cortisol biosensor (916) for measuring changes in Cortisol level. The collected data is pre-processed in (930) before sending both row and pre-processed data to processing function (950). The processing function (950) receives row data in (951) and sends it to (970) storage. The processing function (950) also receives preprocessed data and sends it to training data function (952) and processing data (960). The processing data (960) performs hysteresis tracking (952) and to multi-stage decision (954), it saves the outcome in (970) internal storage and updates (980) the information displayed for the user.

The wellness and wellbeing information system aggregates the collected ambient pollution data and biomarker data to establish a contextual condition of a user that is used to assess the user's stress, fatigue, body's capacity to fight stressors, cardiovascular activities, autonomic coherence to name few of the individualized wellness and wellbeing information available to the users.

Embodiments continuously co-analyzes the potential cause and effect of the ambient pollution condition and changes to the autonomic nervous system (ANS). Although the ANS also responds to various external stimulus i.e. positive and negative emotions, exposure to ambient pollution concentrations in the indoor-space adversely reflect on the users' ANS which is related to many internal organs i.e. stomach, intestine, liver, kidneys, bladder, lungs, pupils, heart, digestive glands, etc., and also regulates many physiological processes i.e. blood flow, heart rate, body temperature, digestion, energy balance, excretion of wastes, fluid volume, electrolyte balance, glucose homeostasis, immune system, inflammatory processes, airway resistance, glandular secretions, papillary diameter, and the list is non-exhaustive.

Embodiments track ambient pollution condition induced changes to the ANS that is derived from the states of its two branches: parasympathetic (PNS) and sympathetic nervous systems (SNS) where multi-stage decision tree (954 FIG. 9) aggregates biomarker data collected using (911 to 916 FIG. 9). Using this data, the embodiment contextualizes ANS trends related to the users' stress condition and energy resilience during their daily routine cycles. The embodiment provides personalized stress condition information to proactively mitigate the risks posed by persistent and unmanaged stress that could become a chronic stress condition. Since unmanaged stress condition could hinder the users to achieve their wellness and wellbeing objectives, the embodiment provides continuous information to raise self-awareness about the users' stress condition. An informed user can take necessary steps to mitigate potential risk factors of developing stress related disorders that could lead to possible disease condition or worsening existing disease conditions.

Embodiments of a wellness and wellbeing information system uses simultaneously collected biomarker data from ECG (911 FIG. 9) and PPG (912 FIG. 9) to provide the users contextualized information about their cardiovascular condition. User specific and customizable information that could be available to the users include blood pressure, heart rate, respiration, blood oxygen saturation, cardiac output, autonomic coherence, microvascular blood flow, vasomotor function, heart rate variability and thermoregulation states. For example, the users with preexisting disease condition could further personalize the information compiled for them to enable them achieving their wellness and wellbeing objectives under their specific condition. Information available to such users could include heart rhythm indicative profile like sinus-rhythm, sinus-tachycardia, sinus-bradycardia, atrial fibrillation, atrial flutter, ventricular tachycardia, ventricular fibrillation. This personalized information is not intended to substitute seeking for appropriate and specialized medical professionals but rather to enable the users to track the biomarker data for their specific condition, to increase their vested interest to maintain wellness and wellbeing condition, and to become more proactive for their condition and promptly seek respective specialized medical doctors' if they find out any trend that needs medical attention before a medical situation arises. The embodiment's aim is to facilitate the user's deliberate effort and to help them to become diligent toward their own wellness and wellbeing objectives.

As another example, wellness and wellbeing information systems use PPG (911 FIG. 9), EDA (913 FIG. 9) and CMC (914 FIG. 9) to collect set of biomarker data to track any changes to the users' baseline condition like the blood flow as a result of underlying diabetic condition that could cause built-up and hardening of the walls of the blood vessels like atherosclerosis, tissue accumulation of AGE (advanced glycosylation end-products) that could indicate potential of the glycemic damage caused by the users' underlying condition. The embodiment also helps the users who are concerned about developing diabetic condition related endothelial dysfunction to track the changes to their baseline condition like their blood vessel dilation that plays a major role in maintaining effective blood flow through blood vessels. The embodiment provides the users means to become aware of given their health condition and to maintain proactive approach to their wellness and wellbeing objective. This inherently includes maintaining their underlying condition under-control, and seeking medical professional attention before developing, for example, diabetic related complications.

Particular embodiments integrated into a protective case for smartphones and handheld devices enables the users through the application interface (App) to participate in a wellness and wellbeing statistical information comparator. The statistical information comparator is intended to facilitate the users to self-compare averages of their own data against similar statistical averages shared by other users. The sharing is completely anonymous and no identifiable personal information is possible for a user to select or to send to the wellness and wellbeing statistical information comparator even if the users desire to do so. For example, the user application interface (App) does not have any field that users could type their name or address or date of birth or any information that could uniquely identify a user, and this information is not also stored in the embodiment. Furthermore, the user application interface (App) protects the data integrity to ensure the accuracy of the shared data for comparison by allowing only the users to select data that is previously collected and the embodiments will calculate the averages before sending for comparison. The embodiment does not allow any data to be manually entered or altered by the users once data is stored in the wellness and wellbeing information system.

A user application interface (App) and the wellness and wellbeing statistical information comparator, in a client-server setup securely compares user provided average data with statistical averages from other users to enable users for self-comparison, and to individually obtain a perspective information of how each user's condition fairs against other users. Embodiments require a consent from the user that once a user sends averages to be compared with other users, the user's average data points become part of the wellness and wellbeing statistical information comparator data that will be used for any future requests from the users. The embodiment's aim is to motivate the users in diligently pursuing their own personal wellness and wellbeing objectives.

For example, the wellness and wellbeing information system's application interface (App) enables users to select data from ambient pollution exposure they had experienced and indicate a particular country to self-compare against the experience of the users in that country. The users will be able to specify a period like a day, a week, a month, three months, six months, etc. Optionally, the users could refine their selection by further selecting a city within this country or even specify a particular indoor-space type like users in multistory apartment buildings or users in houses. Another example, the users could select from any of the monitored ambient pollutants like VOC pollution exposure or PM2.5/PM10 particulate matter pollution exposure experienced to be compared against the experience of other users. Another example, the users could select from the collected ambient data like exposure to electric field radiation pollution, magnetic field radiation pollution, radiofrequency signal radiation pollution and relative humidity of the indoor-space to be compared against similar exposures experienced by other users.

A wellness and wellbeing information system also enables users to self-compare the averages of their physiological biomarkers data stored in the wellness and wellbeing information system against data shared by other users with an enforced scope of the users' anonymity and privacy protection. For example, users could select heart rate and blood pressure to be compared against other users who are physically active or those who indicate they are physically inactive with respect to any physical exercises. Similarly, users could request their selected data to be compared against time specific average data from other user that is collected around the same time of the day like morning between 7:00 am to 9:00 am or any other period of time during the day. For example, users who have preexisting condition like diabetic or hypertension might be interested to compare their average data with data shared by other users having similar preconditions at particular times like before/after daily meals or after waking up or at bedtime. Another example, users could also compare their average heart rate variability (HRV) against other users with the same age group and benefit from the quality of the comparison that will be based on data that is collected and analyzed in the exact same method that achieves high degree of homogeneity among the data set used for the comparison.

If the desired average data is not being shared among the users when a particular user requests with a specific personal data for self-comparison then the embodiments of the wellness and wellbeing information system and the wellness and wellbeing statistical information comparator will respond the user the lack of comparable average data but also provide an alternative comparison by using any available shared data. Instead of the user specified city the comparison will be based on statistical averages of the country, and if no data is available from this country then the continent and eventually compare any available user shared average data around the world. If the wellness and wellbeing statistical information comparator has no such average data from the entire users then the requesting user receives a comparison against a benchmark data that is collected from global research studies and established medical scientific community. The users could also request to compare with the benchmark data instead of user shared averages.

As another example, wellness and wellbeing information systems described herein may be configured to enable users to pre-arrange a third-party like a healthcare provider, or a monitoring control center or a family doctor to send their data stored in the universal holder. Such embodiments require a secured end-to-end data transmission link that has a matching pair of user-interface application (App) for the parties intending to send and receive wellness and wellbeing data. The setup of end-to-end secured link will involve a virtual private network (VPN) between a pair of embodiment's user interface applications (App) where the receiving App could run on any computing platform. This ensures the integrity of the transmitted data to securely reach to only the intended recipient. The embodiment of the user interface application (App) that is set up as a receiving side cannot make remote request and can only receive wellness and wellbeing data sent from a prearranged sender. To further enforce security and privacy of the user data, the receiving App cannot forward to any other entity the data it received from a prearranged sender. The recipient can only either view the data on the user interface application (App) or print it.

A protective case or sleeve for a smartphone or handheld device when setup for physical mode could be used to monitor the status of a lone worker, an elderly, or a disabled person. For example, the user's displacement and any desired ambient pollution condition and the physiological biomarker condition could be collected and sent to a prearranged remote recipient. The user can change or modify the remote third-party recipient which will require the process of reestablishing a prearranged secured communication link. A wellness and wellbeing information system could be configured to periodically alert the users if no change of displacement were detected and then prompt the user to press "ok" on the user-interface application (App) before sending it to the remote monitoring center as a user acknowledged "ok" status. Another example, the user could press "help" option on the user interface application (App) or verbally invoke the "help" option to send distress status to alert the prearranged remote monitoring center.

In an embodiment using the wellness and wellbeing information system (11 FIG. 1A) used as protective case or sleeve for the smartphones and handheld devices, the extension arm-trap (13 FIG. 1C), and remote ambient pollution monitoring (601 FIG. 6) could be used to remotely collect indoor-space ambient pollution condition data and the wellness condition data of an elderly person who is physically inactive that lives alone or in a group living. The collect data could be sent at continuous or at any desired rate to a third party. The embodiment will validate the extension strap attached to either user's arm or leg when activating the physical mode. For example, the embodiment of the wellness and wellbeing information system with extension arm strap collects the elderly user's ambient pollution condition and physiological biomarker condition that it contextualizes the data before sending to a prearranged recipient.

Optionally, the extension arm strap could be equipped with a Bluetooth to enable an elderly person or a disabled person to only wear the extension arm-strap that sends the data via a single-hop or double-hop to a third party. For example, a single-hop Bluetooth connection is in use when separately warn extension strap and the wellness and wellbeing information system are directly paired. However, when the person wearing only the extension strap moves away from the range of the wellness and wellbeing information system then the extension arm could pair with a Bluetooth connection to its closest remote ambient pollution monitor that will relay the data collected from the user via powerline Ethernet connection to the wellness and wellbeing information system that is also paired with its closest remotely ambient pollution monitor. This results a double-hop paring between the extension strap warn by an elderly or disabled person and the wellness and wellbeing information system before sending the data to a prearranged third-party. The remote monitoring center could initiate procedural steps to provide service to the remotely monitored user when abnormalities are detected from the data received from the user.

It will be understood that implementations of a wellness and wellbeing information system are not limited to the specific assemblies, devices and components disclosed in this document, as virtually any assemblies, devices and components consistent with the intended operation of a wellness and wellbeing information system may be used. Accordingly, for example, although particular wellness and wellbeing information systems, and other assemblies, devices and components are disclosed, such may include any shape, size, style, type, model, version, class, measurement, concentration, material, weight, quantity, and/or the like consistent with the intended operation of wellness and wellbeing information systems. Implementations are not limited to uses of any specific assemblies, devices and components; provided that the assemblies, devices and components selected are consistent with the intended operation of a wellness and wellbeing information system.

Accordingly, the components defining any wellness and wellbeing information system may be formed of any of many different types of materials or combinations thereof that can readily be formed into shaped objects provided that the materials selected are consistent with the intended operation of a wellness and wellbeing information system. For example, the components may be formed of: polymers such as thermoplastics (such as ABS, Fluoropolymers, Polyacetal, Polyamide; Polycarbonate, Polyethylene, Polysulfone, and/or the like), thermosets (such as Epoxy, Phenolic Resin, Polyimide, Polyurethane, Silicone, and/or the like), any combination thereof, and/or other like materials; glasses (such as quartz glass), carbon-fiber, aramid-fiber, any combination thereof, and/or other like materials; composites and/or other like materials; metals, such as zinc, magnesium, titanium, copper, lead, iron, steel, carbon steel, alloy steel, tool steel, stainless steel, brass, nickel, tin, antimony, pure aluminum, 1100 aluminum, aluminum alloy, any combination thereof, and/or other like materials; alloys, such as aluminum alloy, titanium alloy, magnesium alloy, copper alloy, any combination thereof, and/or other like materials; any other suitable material; and/or any combination of the foregoing thereof. In instances where a part, component, feature, or element is governed by a standard, rule, code, or other requirement, the part may be made in accordance with, and to comply under such standard, rule, code, or other requirement.

Various wellness and wellbeing information system s may be manufactured using conventional procedures as added to and improved upon through the procedures described here. Some components defining a wellness and wellbeing information system may be manufactured simultaneously and integrally joined with one another, while other components may be purchased pre-manufactured or manufactured separately and then assembled with the integral components. Various implementations may be manufactured using conventional procedures as added to and improved upon through the procedures described here.

It will be understood that methods for manufacturing or assembling wellness and wellbeing information systems are not limited to the specific order of steps as disclosed in this document. Any steps or sequence of steps of the assembly of a wellness and wellbeing information system indicated herein are given as examples of possible steps or sequence of steps and not as limitations, since various assembly processes and sequences of steps may be used to assemble wellness and wellbeing information systems.

It will also be understood that although particular embodiments are described with relation to particular functionality and capabilities for configuring various embodiments of a wellness and wellbeing information system throughout this document, all functionality and features may be incorporated into a single embodiment. Thus, although they are described separately in relation to various particular or specific embodiments, all wellness and wellbeing information system functionality is considered to be included within the embodiments described in relation to FIGS. 1A-1C and FIG. 6.

The implementations of a wellness and wellbeing information system described are by way of example or explanation and not by way of limitation. Rather, any description relating to the foregoing is for the exemplary purposes of this disclosure, and implementations may also be used with similar results for a variety of other applications employing a wellness and wellbeing information system.

What is claimed is:

1. A wellness and wellbeing information system comprising:
   a holder for a protective case and sleeve configured to couple with and protect an electronic handheld device having a user interface, wherein the protective case and sleeve are adjustable to fit each of a plurality of different electronic handheld devices;
   a statistical data comparator configured to communicate with the protective holder to anonymously compare statistical averages of ambient pollution exposures and physiological biomarker data stored in the protective holder to receive a request from a user and to respond an outcome to the user; and
   a sensor device affixed to the protective case, communicatively coupled to the electronic handheld device, and controllable through the user interface, the sensor device having processing function and an internal battery, a plurality of sensors coupled to the internal battery, and controlled airflow through a first vent and a second vent each extending through the sensor device and each configured to supply ambient air to the plurality of sensors, wherein the first vent is perpendicular to the second vent;
   wherein the sensor device is configured to sense an orientation of the protective holder and select one of the first vent and the second vent as a source of ambient air based on which of the first vent and the second vent is closest to a vertical orientation;
   wherein the sensor device is configured to detect any contact of hand-palm or fingertips and select any validated stable contact between the user's hand-palm and fingers and the front-end of the plurality of sensor devices on the perimeter of the protective holder;
   wherein the plurality of sensors is configured to collect data regarding ambient pollution conditions and physiological biomarker conditions of a user and communicate the contextual information to the electronic handheld device;
   wherein the ambient pollution conditions include at least one of ambient airborne pollution, ambient electric field radiation pollution, ambient magnetic field radiation pollution, and ambient radiofrequency signal radiation pollution;
   wherein the physiological biomarker conditions include at least one of a cardiovascular activities, autonomic coherence, respiration, blood oxygen saturation, microvascular blood flow, fingernail cortisol, stress, fatigue, body's capacity to fight stressors and body thermoregulations;
   wherein the information system is configured to operate in at least three operation modes, the operation modes comprising an interactive mode wherein the information system collects data regarding at least one of the ambient pollution conditions and the physiological biomarker conditions in response to a query by the user, a passive mode wherein the information system collects the data regarding at least one of the ambient pollution conditions and the physiological biomarker conditions at predetermined periodic intervals without any user awareness, and a physical mode wherein the information system continuously collects data regarding at least one of the ambient pollution conditions and the physiological biomarker conditions; and
   wherein the information system autonomously collects and processes the data regarding at least one of the ambient pollution conditions and the physiological biomarker conditions at a user configured periodic cycle provided the user is authenticated in passive mode even when the electronic handheld device is turned off, and the user interface (App) is shutdown.

2. The information system of claim 1, further comprising a range extender configured to extend an indoor coverage distance over which the information system is capable of measuring the ambient pollution conditions.

3. The information system of claim 1, further comprising an elastic secured biosensor configured to fit over a finger of the user and provide measurements of the physiological biomarker conditions of the user when the information system is in the interactive mode.

4. The information system of claim 1, further comprising a biosensor strap configured to wrap around a limb of the user, detect an artery within the user, indicate biosensor alignment with the artery, and attach the information system to the user for continuous data collection when the information system is in the physical mode.

5. The information system of claim 1, wherein the information system is configured to communicate user selected data to a pre-arranged third party and provides a secure interface wherein only the user is allowed to send the user selected data to a third party.

6. The information system of claim 1, wherein the user interface is configured to allow the user to set exposure limits for the ambient pollution conditions and alert the user when the exposure limits are reached.

7. The information system of claim 1, wherein the user interface is configured to allow the user to set biomarker ranges for the physiological biomarker conditions and alert the user when a selected physiological biomarker condition is out of range.

8. The information system of claim 1, wherein users' request for comparison of statistical averages of ambient pollution exposures and physiological biomarker conditions stored in their holders are compared with statistical averages pooled from other participating users and benchmark data.

9. A wellness and wellbeing information system comprising:
a sensor device communicatively coupled to an electronic handheld device having a user interface configured to control the sensor device, the sensor device having a plurality of sensors configured to collect data regarding ambient pollution conditions and physiological biomarker conditions of a user and communicate the information to the electronic handheld device; and
a statistical data comparator configured to receive a request to compare a user selected statistical average of ambient pollution exposures and physiological biomarker conditions data with benchmark data within the information, and responds an outcome to the requestor;
wherein the information system is configured to operate in at least one of an interactive mode wherein the information system collects data regarding at least one of the ambient pollution conditions and the physiological biomarker conditions in response to a query by the user, a passive mode wherein the information system collects data regarding the ambient pollution conditions and the physiological conditions at predetermined periodic intervals, and a physical mode wherein the information system continuously collects data regarding at least one of the ambient pollution conditions and the physiological conditions;
wherein the information system is configured to autonomously collect and process data at a user configured periodic cycle provided the user is authenticated in passive mode, and the information system is configured to continue data collection and processing when the electronic handheld device is not paired with the protective holder, the electronic handheld device is turned off, and the user interface (App) is shutdown.

10. The information system of claim 9, further comprising a holder for protective case and sleeve configured to couple with and protect the electronic handheld device, wherein the sensor device is affixed to the protective case and sleeve.

11. The information system of claim 9, wherein the information system is configured to operate in at least two of the interactive mode, the passive mode, and the physical mode.

12. The information system of claim 9, wherein the ambient pollution conditions include at least one of ambient airborne pollution, ambient electric field radiation pollution, ambient magnetic field radiation pollution, and ambient radiofrequency signal radiation pollution.

13. The information system of claim 9, wherein the physiological biomarker conditions include at least one of a cardiovascular activities, autonomic coherence, respiration, blood oxygen saturation, microvascular blood flow, fingernail cortisol, stress, fatigue, body's capacity to fight stressors and body thermoregulation.

14. The information system of claim 9, further comprising a range extender configured to extend the indoor coverage over which the information system is capable of measuring the ambient pollution conditions.

15. The information system of claim 9, wherein the user interface is configured to allow the user to set thresholds for exposure limits for the ambient pollution conditions and physiological biomarker ranges, and alert the user when the thresholds are reached.

\* \* \* \* \*